(12) United States Patent
Bynum et al.

(10) Patent No.: US 7,905,859 B2
(45) Date of Patent: Mar. 15, 2011

(54) PUMP WITH VENTING

(75) Inventors: Gail Beth Bynum, Brooklyn Park, MN (US); Mark Henry Faust, Lino Lakes, MN (US); Jay Gregory Johnson, Maple Plain, MN (US); Clinton S. Vilks, Plymouth, MN (US); William H. Harm, Robbinsdale, MN (US)

(73) Assignee: Smiths Medical ASD, Inc., Rockland, MA (US)

( * ) Notice: Subject to any disclaimer, the term of this patent is extended or adjusted under 35 U.S.C. 154(b) by 0 days.

(21) Appl. No.: 11/680,871

(22) Filed: Mar. 1, 2007

(65) Prior Publication Data

US 2007/0161955 A1  Jul. 12, 2007

Related U.S. Application Data

(60) Continuation of application No. 11/152,880, filed on Jun. 15, 2005, now Pat. No. 7,510,544, which is a division of application No. 10/086,646, filed on Feb. 28, 2002, now Pat. No. 7,033,338.

(51) Int. Cl.
*A61M 37/00* (2006.01)
(52) U.S. Cl. ........................................................ 604/131
(58) Field of Classification Search ............... 604/93.01, 604/131, 151–155, 199
See application file for complete search history.

(56) References Cited

U.S. PATENT DOCUMENTS

| | | |
|---|---|---|
| 3,344,787 A | 10/1967 | Maclean |
| 4,365,626 A | 12/1982 | House |
| 4,424,720 A | 1/1984 | Bucchianeri |
| 4,493,704 A | 1/1985 | Beard et al. |
| 4,585,439 A | 4/1986 | Michel |
| 4,675,018 A | 6/1987 | Harden |
| 4,731,058 A | 3/1988 | Doan |
| 4,931,041 A | 6/1990 | Faeser |
| 5,059,179 A | 10/1991 | Quatrochi et al. |
| 5,080,653 A | 1/1992 | Voss et al. |
| 5,084,017 A | 1/1992 | Maffetone |
| 5,097,122 A | 3/1992 | Colman et al. |
| 5,106,375 A | 4/1992 | Conero |
| 5,279,569 A | 1/1994 | Neer et al. |
| 5,322,511 A | 6/1994 | Armbruster et al. |
| 5,336,189 A | 8/1994 | Sealfon |

(Continued)

FOREIGN PATENT DOCUMENTS

EP    0 170 009 A1    2/1986

(Continued)

OTHER PUBLICATIONS

"Animas Pump User Guide," Animas Corporation, 60 pages (Date Unknown).

(Continued)

*Primary Examiner* — Theodore J Stigell
(74) *Attorney, Agent, or Firm* — Patterson Thuente Christensen Pedersen, P.A.

(57) ABSTRACT

A medication pump includes a housing including an external wall and a plurality of internal adjoining housings, including a first housing enclosing a cartridge. The pump includes a primary vent for venting the medication pump to atmosphere, the primary vent including a primary liquid barrier allowing passage of gas therethrough while preventing passage of liquid therethrough. The pump includes a secondary vent on the first housing, the secondary vent including a secondary liquid barrier allowing passage of gas therethrough to an interior of the housing while preventing passage of liquid therethrough.

18 Claims, 29 Drawing Sheets

U.S. PATENT DOCUMENTS

| | | | |
|---|---|---|---|
| 5,395,339 | A | 3/1995 | Talonn et al. |
| 5,456,669 | A | 10/1995 | Neer et al. |
| 5,490,842 | A | 2/1996 | Volk et al. |
| 5,505,709 | A | 4/1996 | Funderburk et al. |
| 5,634,903 | A | 6/1997 | Kurose et al. |
| 5,637,095 | A | 6/1997 | Nason et al. |
| 5,688,252 | A | 11/1997 | Matsuda et al. |
| 5,722,956 | A | 3/1998 | Sims et al. |
| 5,738,659 | A | 4/1998 | Neer et al. |
| 5,741,232 | A | 4/1998 | Reilly et al. |
| 5,919,167 | A | 7/1999 | Mulhauser et al. |
| 5,925,018 | A | 7/1999 | Ungerstedt |
| 5,928,201 | A | 7/1999 | Poulsen et al. |
| 5,947,935 | A | 9/1999 | Rhinehart et al. |
| 5,954,697 | A | 9/1999 | Srisathapat et al. |
| 5,968,017 | A | 10/1999 | Lampropoulos et al. |
| 5,971,963 | A | 10/1999 | Choi |
| 5,993,411 | A | 11/1999 | Choi |
| 5,993,421 | A | 11/1999 | Kriesel |
| 5,993,423 | A | 11/1999 | Choi |
| 6,083,201 | A | 7/2000 | Skinkle |
| 6,090,064 | A | 7/2000 | Reilly et al. |
| 6,090,080 | A | 7/2000 | Jost et al. |
| 6,113,578 | A | 9/2000 | Brown |
| 6,193,698 | B1 | 2/2001 | Kirchhofer et al. |
| 6,248,093 | B1 * | 6/2001 | Moberg ................ 604/131 |
| 6,249,717 | B1 * | 6/2001 | Nicholson et al. ........... 700/241 |
| 6,270,481 | B1 | 8/2001 | Mason et al. |
| 6,305,908 | B1 | 10/2001 | Hermann et al. |
| 6,382,204 | B1 | 5/2002 | Jansen et al. |
| 6,394,983 | B1 | 5/2002 | Mayoral et al. |
| 6,423,035 | B1 | 7/2002 | Das et al. |
| 6,585,695 | B1 | 7/2003 | Adair et al. |
| 6,652,493 | B1 | 11/2003 | Das |
| 6,800,071 | B1 * | 10/2004 | McConnell et al. .......... 604/155 |
| 7,033,338 | B2 | 4/2006 | Vilks et al. |
| 7,510,544 | B2 | 3/2009 | Vilks et al. |
| 2001/0011163 | A1 | 8/2001 | Nolan, Jr. et al. |
| 2001/0056259 | A1 | 12/2001 | Skinkle et al. |
| 2002/0128594 | A1 | 9/2002 | Das et al. |
| 2002/0128606 | A1 | 9/2002 | Cowan et al. |
| 2003/0163089 | A1 | 8/2003 | Bynum |
| 2003/0163090 | A1 | 8/2003 | Blomquist et al. |

FOREIGN PATENT DOCUMENTS

| | | |
|---|---|---|
| WO | WO 96/14893 | 5/1996 |
| WO | WO 01/56635 A1 | 8/2001 |
| WO | WO 03/074110 | 9/2003 |

OTHER PUBLICATIONS

"A-TRONplus Reference Manual," Disetronic Medical Systems, Inc., 103 pages (1999).

"CADD-Micro® Ambulatory Infusion Pump, Model 5900 Operator's Manual," SIMS Deltec, Inc., 91 pages (1996).

"Disetronic Easyfill Instructions For Use," Disetronic Medical Systems Inc., 4 pages (Date Unknown).

"Disetronic Pen Instructions for Use," Disetronic Medical Systems, Inc., 15 pages (Date Unknown) (Color Copy).

"D-TRON™ Insulin Pump Reference Manual," Disetronic Medical Systems Inc., pp. 1-159 (Date Unknown).

"MiniMed® 508 User's Guide," Sylmar, CA, 78 pages (Apr. 1999).

"Quick Start Manual for Dahedi Insulin Pumps by Disetronic," pp. 1-43 (Date Unknown).

"Technical Manual CADD-Micro® Model 5900 Ambulatory Infusion Pump," SIMS Deltec, Inc., pp. 1-22 (Jun. 1995).

Exhibits A-C are photos of a Disetronic D-TRON Insulin Pump (Date Unknown) (Color Copy).

International Search Report for International Application No. PCT/US2003/06203 dated Jun. 10, 2003.

European Office Action for European Application No. 03 713 795.7 dated Dec. 12, 2006. 3 pages.

Application and File History for U.S. Appl. No. 10/086,646, filed Feb. 28, 2002, inventor Vilks et al., at www.uspto.gov.

Application and File History for U.S. Appl. No. 11/152,880, filed Jun. 15, 2005, inventor Vilks et al., at www.uspto.gov.

US 5,954,699, 09/1999, Jost et al. (withdrawn)

\* cited by examiner

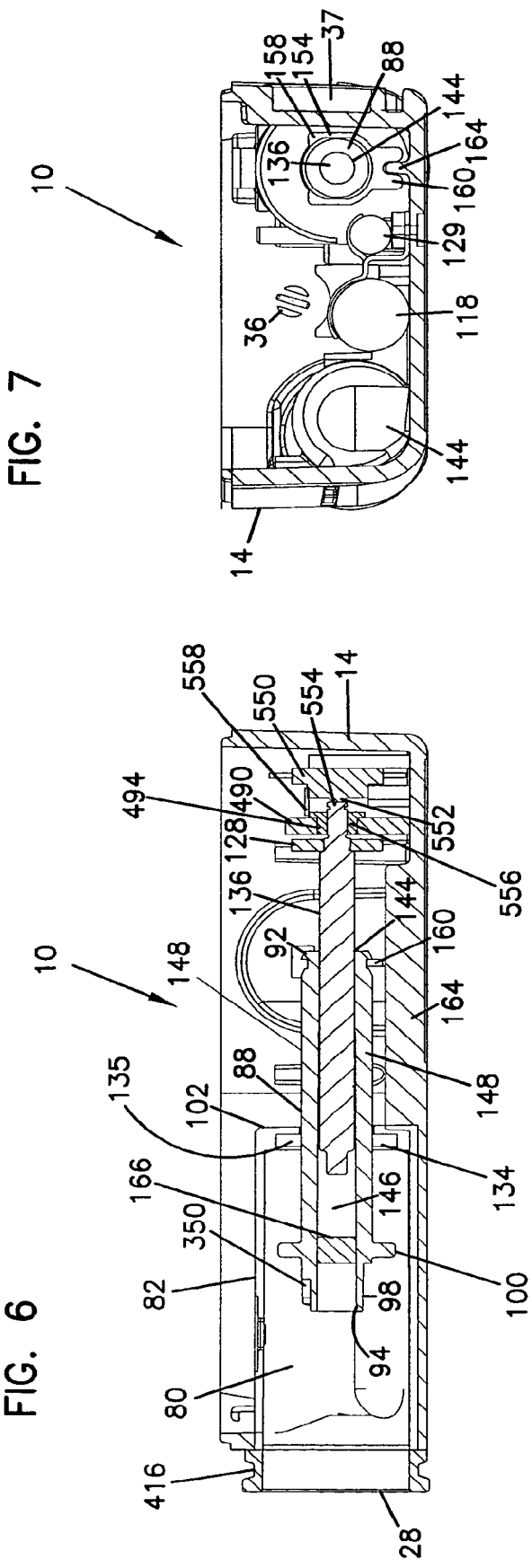

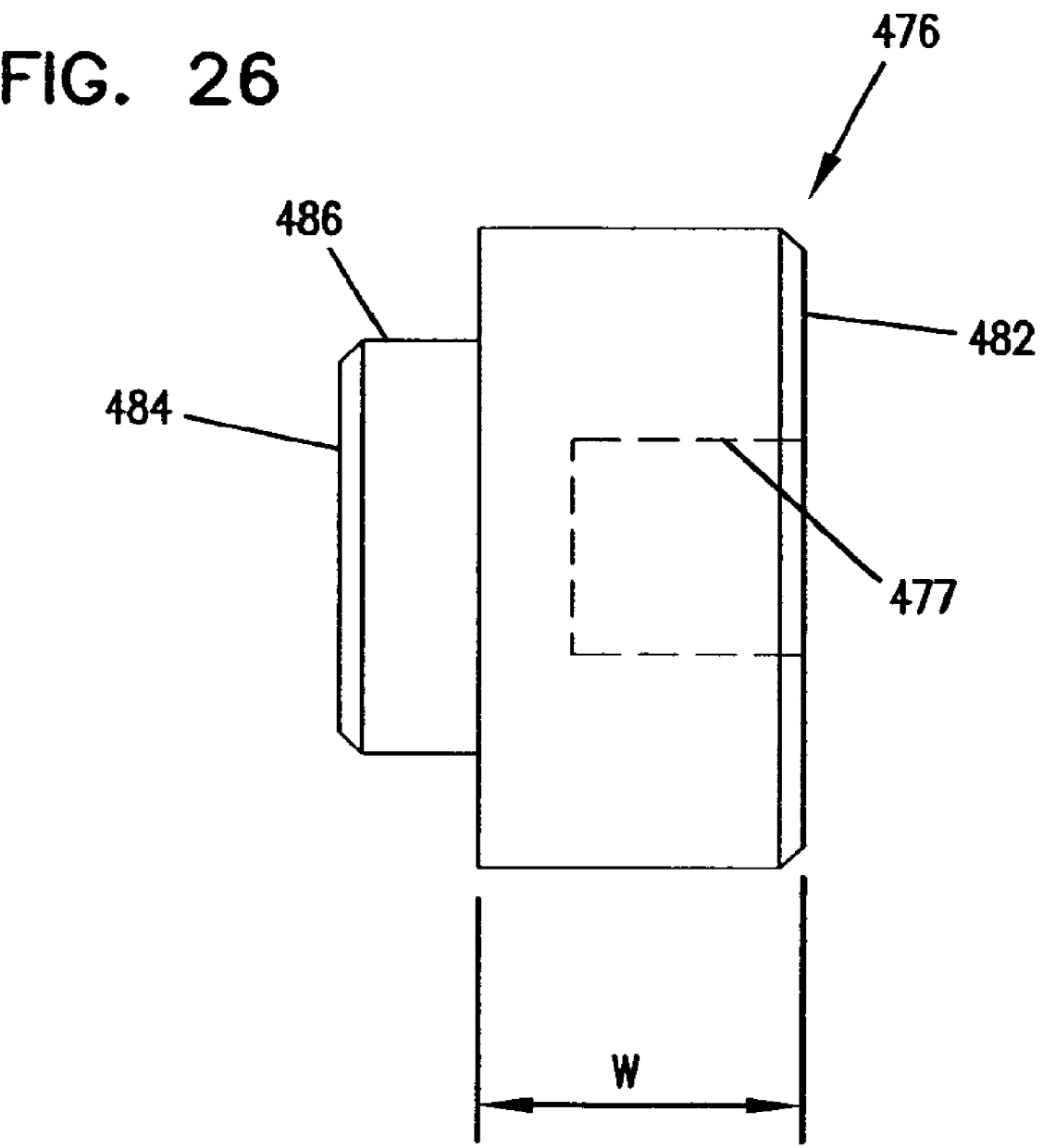

PUMP WITH VENTING

REFERENCE TO CO-PENDING APPLICATIONS

This application is a continuation application of U.S. patent application Ser. No. 11/152,880, filed Jun. 15, 2005, now U.S. Pat. No. 7,510,544, issued Mar. 31, 2009, which is a divisional application of U.S. patent application Ser. No. 10/086,646, filed Feb. 28, 2002, now U.S. Pat. No. 7,033,338, issued Apr. 25, 2006, both of which are hereby incorporated herein in their entireties.

This application is also related to the following six commonly assigned patent applications, which were all filed on Feb. 28, 2002: "Syringe Pump Control Systems and Methods" U.S. application Ser. No. 10/086,994, now U.S. Pat. No. 7,041,082 issued May 9, 2006, "Child Safety Cap for Syringe Pump" U.S. application Ser. No. 10/086,993, now abandoned, "Insulin Pump Having Missed Meal Bolus Alarm" U.S. application Ser. No. 10/087,460, now U.S. Pat. No. 6,744,350 issued Jun. 1, 2004, "Programmable Medical Infusion Pump Displaying a Banner" U.S. application Ser. No. 10/087,205, "Programmable Insulin Pump" U.S. application Ser. No. 10/086,641, now U.S. Pat. No. 6,852,104 issued Feb. 8, 2005, and "Programmable Medical Infusion Pump" U.S. application Ser. No. 10/087,449. The disclosures of these six patent applications are hereby incorporated herein by reference in their entirety.

FIELD AND BACKGROUND OF THE INVENTION

The present invention relates to a medication pump and a cartridge for use in a medication pump, and methods for using the same. More particularly, the present invention is particularly useful in the context of portable medication pumps that automatically discharge medication from a medication cartridge.

Various ambulatory or portable medical devices are known for treating patients at a remote site away from the caregiver or clinician office. One example of an ambulatory medical device is a drug delivery device, such as a drug pump, for providing periodic or continuous drug delivery to the patient when the patient is away from the caregiver's office. Ambulatory drug pumps are shown for example in U.S. Pat. Nos. 4,559,038, 4,731,058, 5,531,697, 5,389,078 and 5,695,473, the disclosures of which are hereby incorporated by reference. Drug pumps may be used to deliver insulin and many other medications.

Medication pumps are known that use a piston-like arrangement to push medication out of a cylindrical medication reservoir. The cylindrical medication reservoir may be provided within a cylindrical barrel, where a plunger pushes medication out of the reservoir, and may be called a syringe or cartridge. Drug pumps typically have a delivery conduit for connecting to the patient's body for delivery of the drug. An infusion set typically includes the delivery conduit, an access device for attaching the delivery conduit to the patient's body and an attachment device for attaching the delivery conduit to a medication cartridge. Improved structures and methods are needed for filling medication cartridges, loading medication cartridges, and sensing conditions within medication pumps.

SUMMARY OF THE INVENTION

The present invention concerns a medication pump, a cartridge for use in a medication pump, a pump cap for use with a medication pump, components of the cartridge and methods of use of these devices.

A cartridge for use in a medication pump includes a cylindrical barrel and a plunger slidably received within the barrel, where the plunger includes a first tab projecting inwardly from an interior wall face. Preferably the cartridge also includes a removable cartridge rod including a shaft and an interface cylinder at one end of the shaft, where the interface cylinder defines a first channel for receiving and retaining the first tab of the plunger. The first channel of the interface cylinder preferably includes an axial portion disposed parallel to an axis of the shaft and a locking portion disposed in a circumferential direction around an outer surface of the interface cylinder. The cartridge may also include axial guides at a closed end.

A cartridge barrel for use in a medication pump includes a cylindrical barrel wall with an open end and a closed end, where the closed end defines an orifice. The cartridge barrel also includes a cylindrical end wall projecting from the closed end of the cylindrical barrel wall and surrounding the orifice, where the end wall includes an interior face, an exterior face, and axial guides on the exterior face.

A plunger for use within a medication cartridge in a medication pump includes a cylindrical plunger wall having an interior cylindrical wall face and a first tab projecting inwardly from the interior wall face. Preferably, the plunger also includes a second tab projecting inwardly from the interior wall face positioned opposite the first tab.

A removable cartridge rod for use with a medical cartridge in a medical pump includes a shaft and an interface cylinder at the one end defining a first channel. The first channel includes an axial portion disposed parallel to an axis of the shaft and a locking portion disposed in a circumferential direction around an outer surface of the interface cylinder. Preferably, the interface cylinder also defines a second channel for receiving and retaining a portion of a plunger. The second channel also includes an axial portion disposed parallel to the axis of the shaft and a locking portion disposed in a circumferential direction around the outer surface of the interface cylinder.

Another medication cartridge for use in a medication pump includes a cartridge barrel comprising an open end and a closed end, wherein the closed end defines an orifice. The cartridge barrel also includes a cylindrical end wall projecting from the closed end and surrounding the orifice, the end wall having an interior face, an exterior face, and axial guides on the exterior face. A plunger is slidably received within the barrel. A medication pump includes a motor, a cartridge chamber for receiving a medication cartridge, and a drive rod extending into the cartridge chamber through the drive rod opening, where the drive rod is configured to be axially moved by the motor. The drive rod includes an interface structure at one end, where the interface structure defines a first channel. The first channel includes an axial portion disposed parallel to an axis of the drive rod and a locking portion disposed in a circumferential direction around an outer surface of the interface structure. This pump may be used with a medication cartridge that has a plunger including a first tab projecting inwardly from an interior wall face, and the first tab may be received in the first channel to lock the plunger to the drive rod. Preferably, the interface structure also defines a second channel comprising an axial portion disposed parallel to the axis of the drive rod and a locking portion disposed in a circumferential direction around the outer surface of the interface structure. This second channel can receive a second tab on the plunger, in a preferred configuration. The interface structure of the drive rod may include a visual indicator, wherein when the interface structure is coupled to a plunger, the visual indicator is positioned within the plunger. The pump may include a window in its outer housing that allows a view into the cartridge chamber.

The medication pump may include a pump cap configured to rotationally attach to an open end of the cartridge chamber to close the cartridge chamber, where the pump cap has an interior surface including guides that engage axial guides at a closed end of the medication cartridge. When the pump cap is rotated into engagement with the open end of the cartridge chamber, the cartridge is rotated in a first direction to move the tab into the locking portion of the channel on the drive rod interface structure.

The present invention also includes a medication pump having a motor, a cartridge chamber for receiving a medication cartridge, and a drive rod having an interface structure at one end that extends into the cartridge chamber through an end of the cartridge housing. The drive rod is configured to be axially moved by the motor. The interface structure includes a visual indicator, so that when the interface structure is coupled to a plunger of a medication cartridge, the visual indicator is positioned within the plunger. The pump also includes an outer housing having a window into the cartridge chamber that allows a view of the visual indicator.

A method of filling a medication cartridge with fluid includes a attaching fill rod to a plunger by inserting an interface end of the rod into an interior cylinder of the plunger axially and rotating the rod in a first direction so that a tab of the plunger is moved into a locking portion of a channel of the interface end of the rod. Then the plunger is retracted within the barrel by pulling on the rod to draw fluid into the barrel. Then the rod is detached from the plunger by rotating the rod in a second direction opposite the first direction and withdrawing the rod from the interior cylinder of the plunger.

Another method according to the present invention is a method of locking a medication cartridge into a pump involving inserting the cartridge axially into a cartridge chamber so that a tab of a plunger travels along an axial portion of the channel of the drive rod. Then the cartridge is rotated in a first direction so that the tab travels along a locking portion of the channel in the drive rod.

Another medication pump system according to the present invention includes a pump cap for rotationally attaching to an open end of a cartridge chamber to close the cartridge chamber, where the pump cap comprising guides located on an interior surface. These guides engage axial guides at a closed end of a medication cartridge, so that when the pump cap is rotated into engagement with the open end of the cartridge chamber, the cartridge is rotated into engagement with an interface structure of a drive rod.

The present invention also involves a method of locking a medication cartridge into a pump, where the cartridge is axially inserted into the cartridge chamber and a pump cap is rotated into engagement with an open end of a cartridge chamber. The rotation of the pump cap causes guides on an interior surface of the pump cap to interact with axial guides on the cartridge so that the cartridge is rotated, whereby the plunger is rotated into engagement with the drive rod.

BRIEF DESCRIPTION OF THE DRAWINGS

The invention may be more completely understood by considering the detailed description of various embodiments of the invention which follows in connection with the accompanying drawings.

FIG. 6 is a cross-sectional view of the components of FIG. 5 along line 6-6 of FIG. 5.

FIG. 7 is a cross-sectional view of the components of FIG. 5 along line 7-7 of FIG. 5.

FIG. 26 is a side view of a bushing used to space the idler gear from the idler gear sensor according to one embodiment of the present invention.

Figure 1:
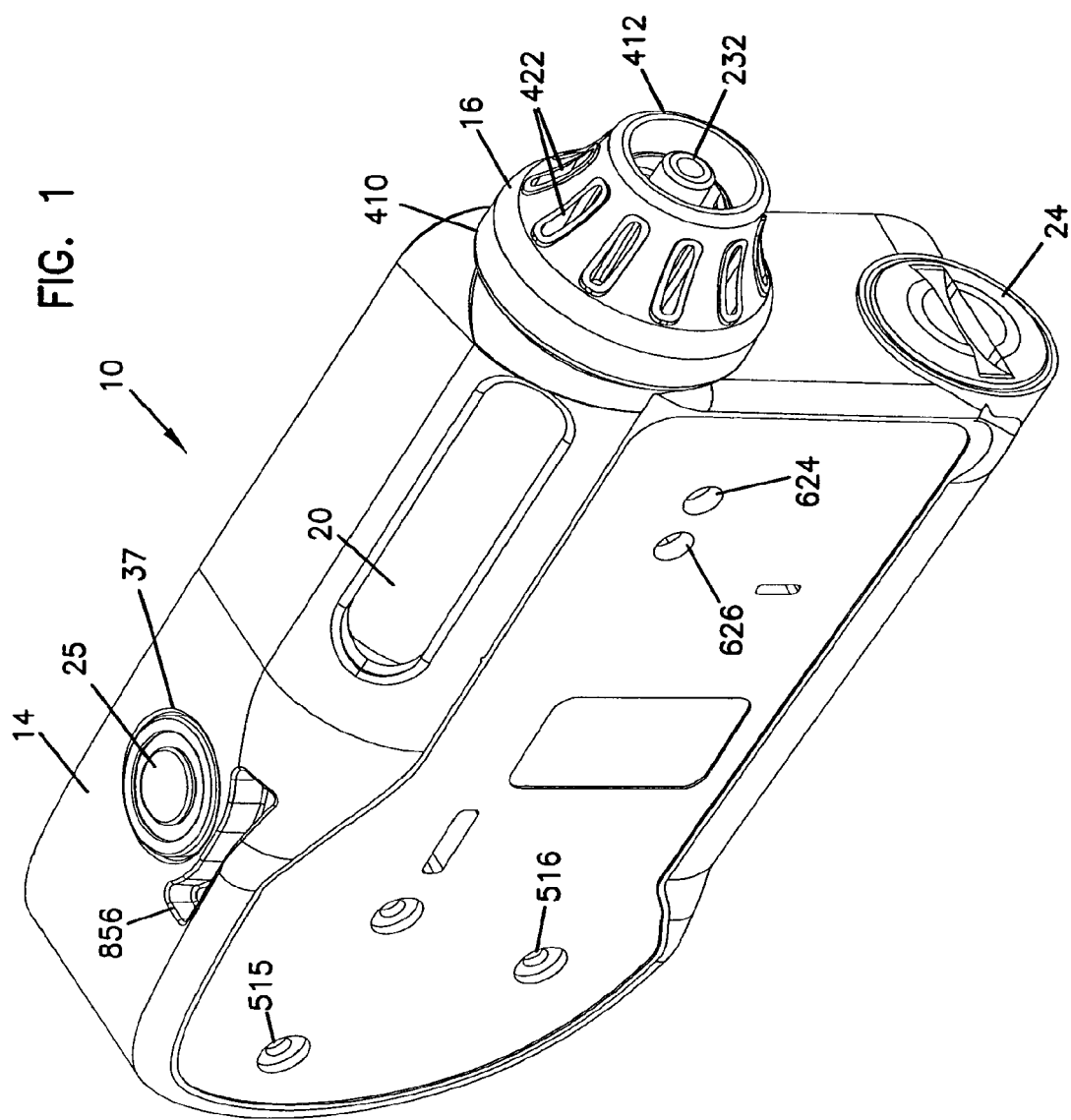
FIG. 1 is a back, left perspective view of a syringe pump according to one embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE VARIOUS EMBODIMENTS

The present invention is believed to be applicable to a variety of devices, systems and methods for delivering medication using a syringe or cartridge and a pump. The invention has been found to be particularly advantageous in application environments where a cartridge is axially loaded into a pump. While the present invention is not so limited, an appreciation of various aspects of the invention is best gained through a discussion of various application examples operating in such an environment.

Various embodiments of the present invention will be described in detail with reference to the drawings, where like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

FIG. 1 illustrates one particular embodiment of a syringe pump where a syringe or cartridge is axially loaded. The terms syringe and cartridge will be used interchangeably to refer to a device having a hollow barrel fitted with a plunger. The pump 10 of FIG. 1 includes an outer pump housing 14. A pump cap 16 covers an opening into a cartridge chamber 80 (shown in FIG. 4) that receives a syringe or cartridge. The pump outer housing 14 also includes a viewing window 20 into the cartridge chamber. The pump 10 also includes a battery cover 24.

Figure 2:
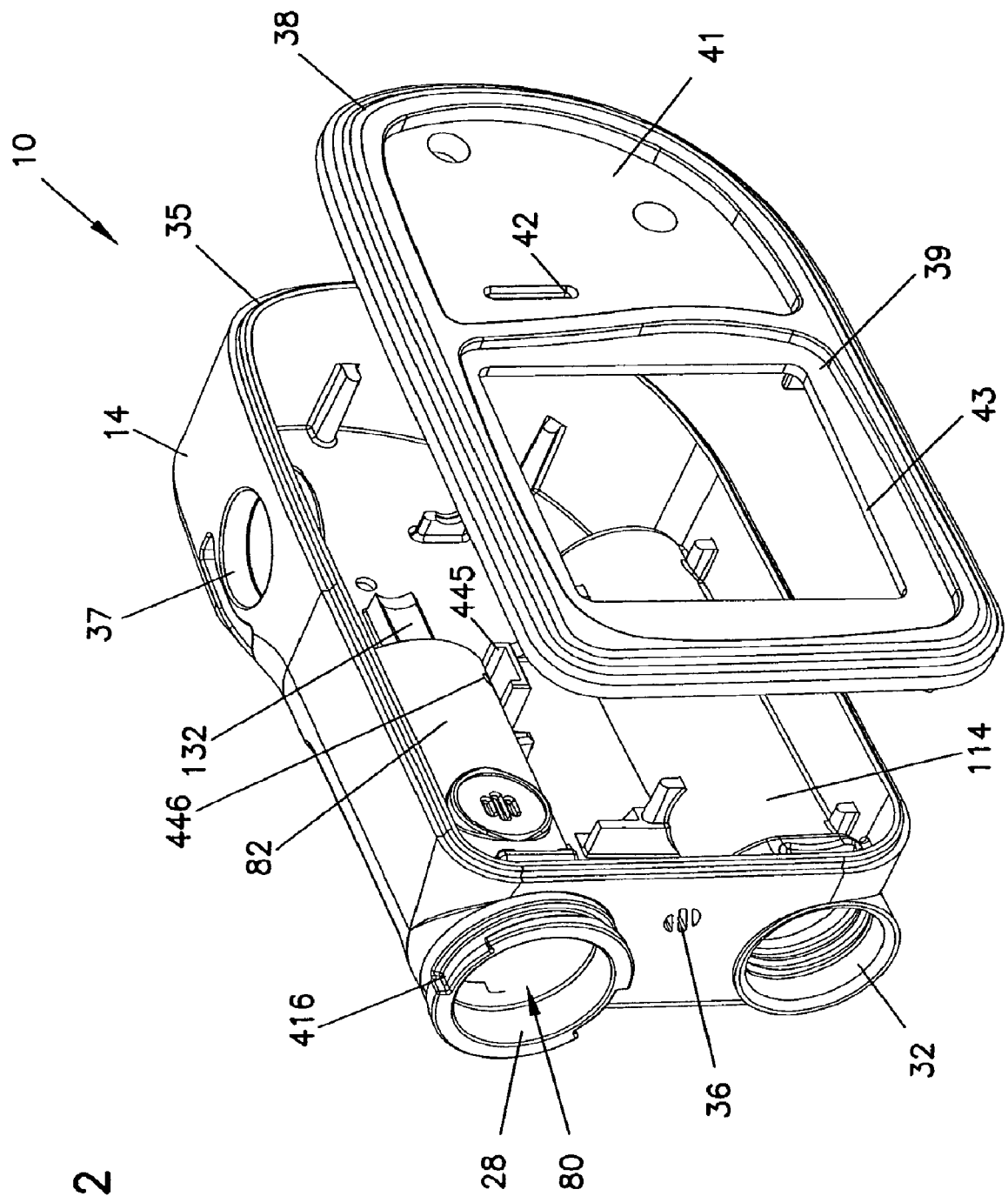
FIG. 2 is a front, left perspective view of a housing of the pump of FIG. 1 with the bolus button, battery cap and pump cap removed, with the front cover separated from the housing.

Now referring to FIG. 2, the pump 10 is shown without the pump cap 16, revealing the opening 28 to the chamber 80. In addition, the battery cap 24 is removed in the view shown in FIG. 2, revealing the battery chamber opening 32. A front panel 38 is shown removed from the remainder of the pump housing 14, allowing a view into the interior of the pump housing 14. The drive assembly components and circuit boards of the pump 10 are removed from the pump housing 14 in the view shown in FIG. 2. A cylindrical chamber wall 82 surrounds the cartridge chamber 80. The battery chamber 114 is positioned adjacent to the battery opening 32.

The front panel 38 defines a depression 39 for receiving a lens and an opening 43 for a display screen. The front panel 38 also defines a depression 41 for receiving a keypad and an opening 42 for facilitating an electrical connection to the keypad.

A vent 36 is visible in FIG. 2 on the right end of the pump outer housing 14. The vent 36 preferably incorporates a water barrier that is air permeable so that moisture is not allowed into the interior of the pump, but pressure equalization is possible between the interior and exterior of the pump. The use of a water barrier in vent 36 allows pressure equalization of a sealed environment within the pump housing 14. The water barrier may be attached to an interior surface of the pump housing 14 using a pressure sensitive adhesive. Adhesive capable of a water tight seal may be provided along perimeter 35 of pump housing 14 to bond the pump housing 14 to the front panel 38 so that the pump 10 can be exposed to water without allowing water into the pump interior.

Figure 3:
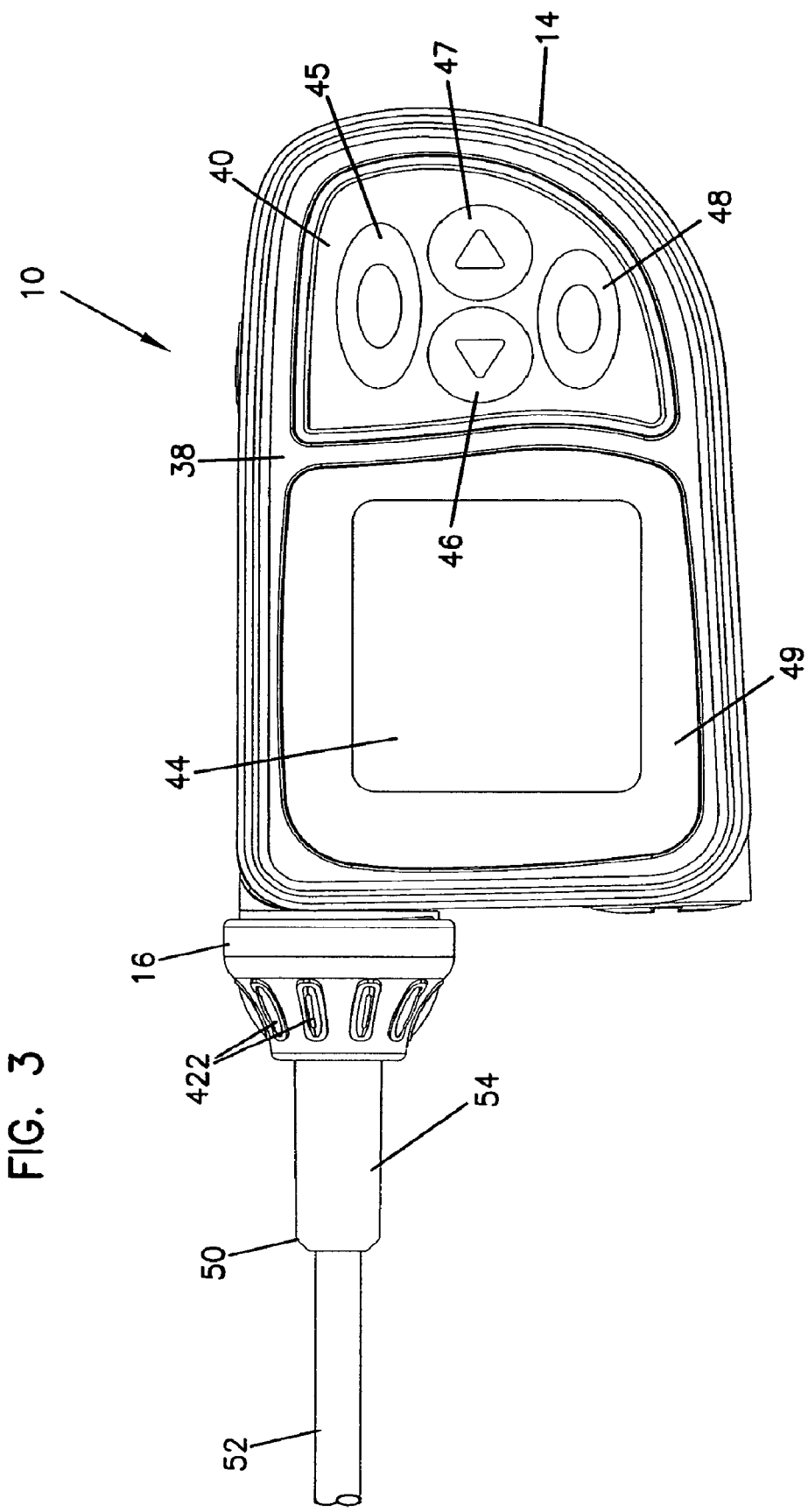
FIG. 3 is a front view of the pump of FIG. 1 showing the keypad and display screen, where the pump is attached to an administration set.

Now referring to FIG. 3, the front panel 38 of the pump 10 is shown including a keypad 40 with individual buttons 45-48 for allowing a user to input information and make menu choices. The front panel 38 also includes a display 44 present behind a lens 49, within the opening 43. In FIG. 3, an administration set is shown emerging from the pump cap 16. The administration set includes tubing 52 for delivering medication to the body of a patient or user. The administration 50 also includes a connector 54 for attaching the tubing to a medication cartridge within the pump. Often, a luer-lock connection is used between the administration set 50 and the medication cartridge.

Figure 4:
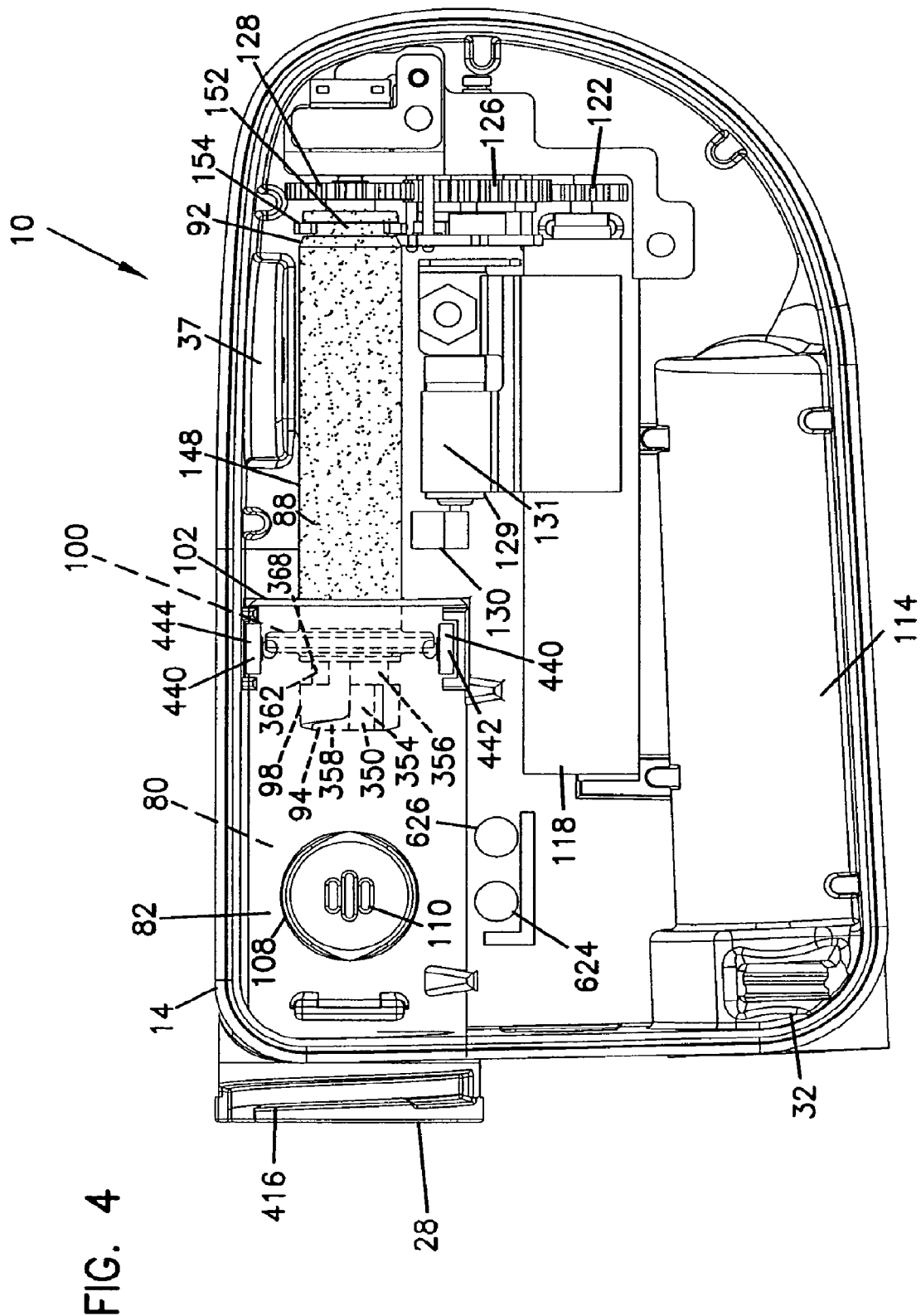
FIG. 4 is a front view of the drive assembly components within the pump housing for the pump of FIG. 1.

Now referring to FIG. 4, a front view of some of the components of the pump 10 within the pump housing 14 is shown, where the front panel 38 has been removed. The cartridge opening 28 opens into the cartridge chamber 80. FIG. 4 shows a top view of the exterior wall 82 of the cartridge chamber 80. The cartridge chamber is where cartridges or syringes of medication are placed for delivery to the patient. A drive rod 88 is configured to move axially to dispense medication from a cartridge in the cartridge chamber 80. The drive rod has a first end 92 and a second end 94. At the second end 94 of the drive rod 88 an interface cylinder 98 is defined for coupling to a plunger of a medication cartridge. A drive rod flange 100 is present at the second or distal end 94 of the drive rod 88, and adjacent to the interface cylinder.

The cartridge chamber 80 includes an open end at the cartridge opening 28 and a closed end 102 opposite the cartridge opening 28. The closed end 102 of the cartridge chamber 80 defines an opening for allowing the drive rod 88 to enter the cartridge chamber. The cartridge chamber also includes a vent 108. The vent includes openings 110 to allow for the passage of gas between the cartridge chamber 80 and the interior of the pump housing. The vent 108 may also include a gas permeable water barrier that covers the openings 110, similar to vent 36. Preferably, the vent 108 allows for pressure equalization between the chamber 80 and the pump interior but prevents the passage of fluid. A watertight vent between the cartridge chamber 80 and the interior of the pump is valuable because the pump components will not be exposed to any fluid in the cartridge chamber, for example, if fluid leaks from a medication cartridge.

The pump 10 also includes a battery chamber 114 having an open end at the battery opening 32 that is closeable using the battery cover 24. A battery within the battery chamber 114 is electrically connected to a motor 118. The motor rotates a motor gear 122. An idler gear 126 is in turn rotated by the motion of the motor gear 122. The idler gear interacts with a drive rod gear 128 causing the drive rod gear to rotate when the idler gear 126 is rotated. The pump may also include a vibratory motor 129 with a protruding structure 130 that is moved by the motor 129. The vibratory motor 129 can be used to call the user's attention to the device. An audible signal may also be used to attract the user's attention, alone or in combination with a vibration. A bracket 131 holds the driving motor 118 and the vibratory motor 129 in place in the pump housing. A mount structure 132 for the vibratory motor is shown in FIG. 2.

In FIG. 4, the drive rod 88 is fully retracted, so that its first end 92 is as close to the drive rod gear 128 as possible. In this fully retracted position, the interface cylinder is as close as possible to the interior face of closed end 102 of the cartridge chamber. Preferably, the flange 100 is contacting the chamber's closed end 102 when the drive rod 88 is in the fully retracted position.

The interior face 134 of the closed end 102 is shown in FIG. 6. The closed end 102 defines a cavity 135 for holding an elastomeric sealing member (not shown) to seal the opening in the closed end through which the drive rod passes. The drive rod flange 100 will preferably contact the sealing member within the cavity 135 in the closed end 102 of the cartridge chamber 80.

Figure 5:
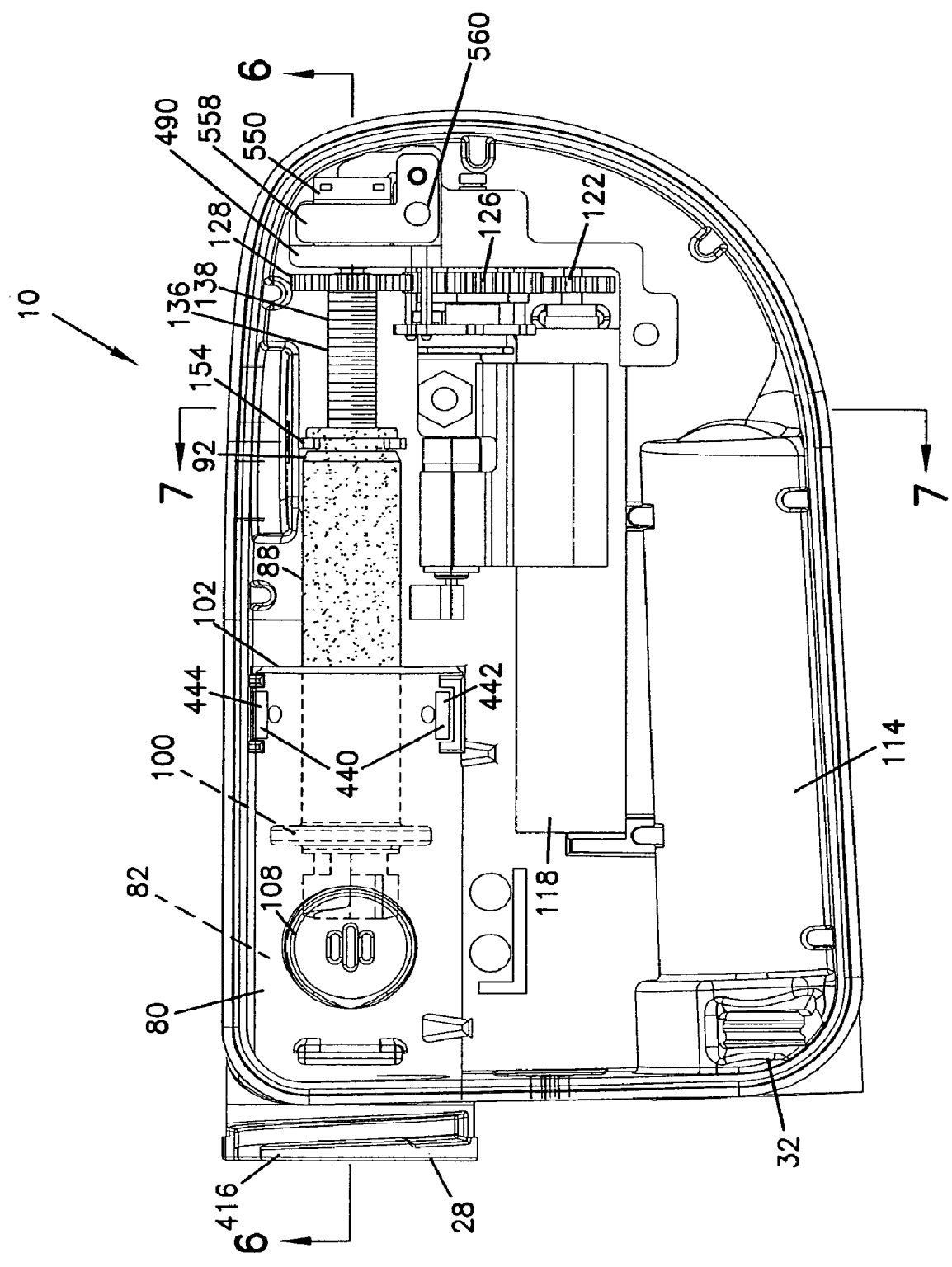
FIG. 5 is a front view of the drive assembly components within the pump housing for the pump of FIG. 1 where the drive rod is partially advanced into the cartridge chamber.

FIG. 5 shows a front view of the components of the pump 10 similar to FIG. 4 but where the drive rod is at a different position. In FIG. 5, the drive rod 88 is partially extended into the cartridge chamber 80.

Figure 34:
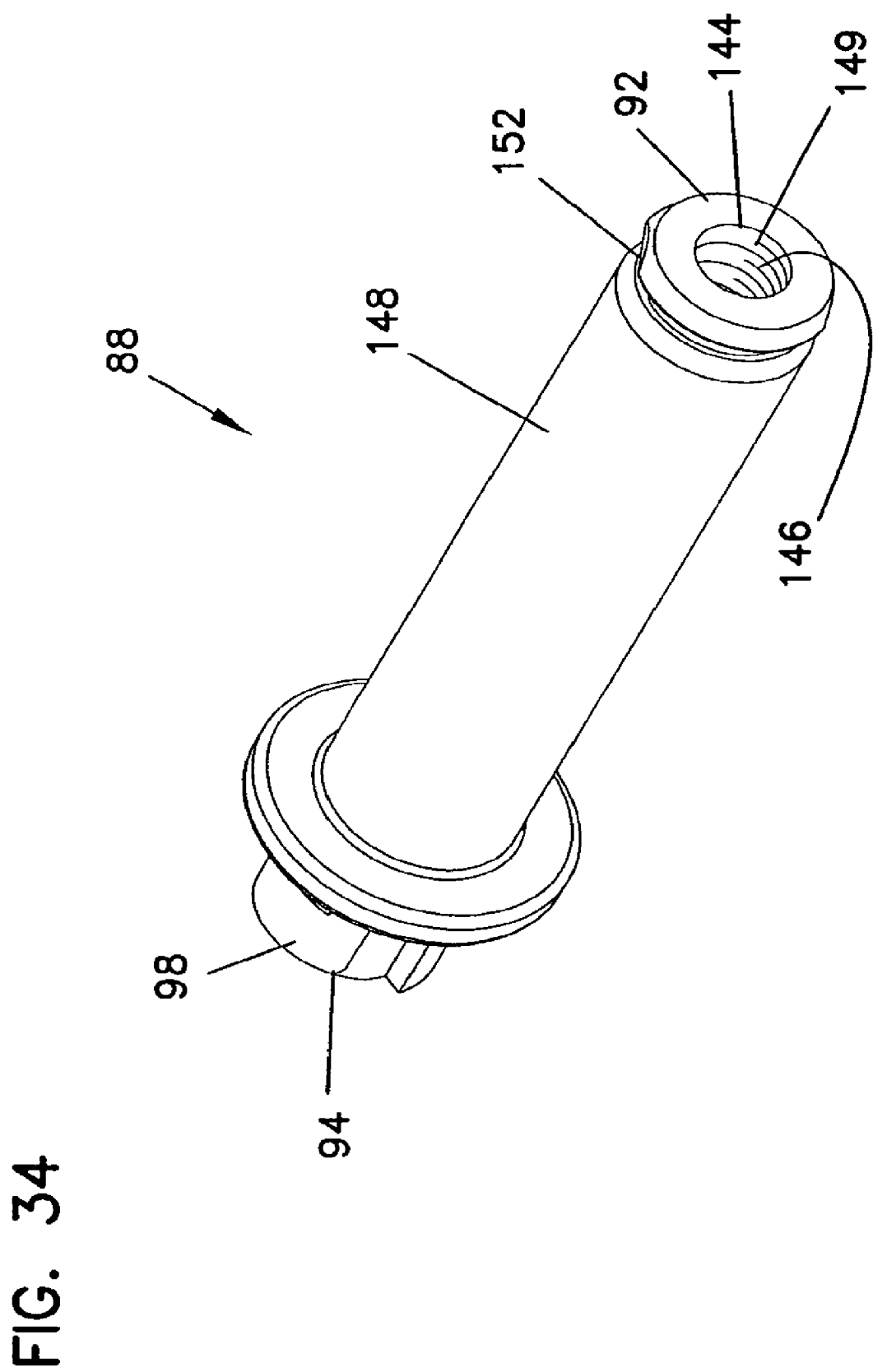
FIG. 34 is a right perspective view of the drive rod of FIG. 8.

When the motor 118 operates, the drive rod gear 128 is rotated and the drive rod 88 is axially moved. A lead screw 136 is connected to the drive rod gear 128 and is rotated when the drive rod gear 128 is rotated. The lead screw 136 includes threads 138 on its outer surface. As can be seen in FIGS. 6-7 and 34, the first end 92 of the drive rod 88 includes an opening 144 for receiving the lead screw 136. The lead screw 136 is received within the drive rod opening 144 and extends within an interior 146 of the drive rod 88. The drive rod 88 includes a cylindrical shaft 148 and defines a cylindrical interior chamber 146. At the first end 92 of the drive rod 88, threads 149 are defined on the interior surface of the drive rod 88 for interacting with the threads 138 of the lead screw 136.

The drive rod 88 does not rotate as it is axially moved. Preventing the drive rod from rotating as it is axially moved is important because if the drive rotates, it will not be axially moved by the rotation of the lead screw. The drive rod 88 is held in a fixed orientation by a clip 154 that interacts with the outer housing 14. The drive rod 88 includes a recessed portion 152 at the first end 92. The clip 154 attaches to the drive rod 88 at the recessed portion 152. The clip 154 prevents the drive rod 88 from rotating when the lead screw 136 is rotated. As best seen in FIG. 7, the clip 154 includes a U-shaped portion 158 that fits around the recessed portion 152 of the drive rod 88. The clip 154 also includes a downward extension 160 that rides on a rib 164. The rib 164 is a part of the pump housing 14 and extends along the length of the drive rod and lead screw from the drive rod gear 128 to the closed end 102 of the cartridge chamber 80. When the lead screw 136 rotates, the threads 149 at the opening 144 at the first end 92 of the drive rod 88 ride along the threads 138 of the lead screw 136, causing the drive rod 88 to be axially moved.

Preferably, the interior chamber 146 of the drive rod 88 does not extend all the way through the drive rod 88 from the first end 92 to the second end 94. As seen in FIG. 6, preferably a closure 166 is present within the interior 146. The closure 166 may be molded into the structure of the drive rod 88 when the drive rod is manufactured. Alternatively, a plug structure may be inserted into the interior 146 to provide the closure 166. The closure 166 prevents any moisture or fluid from traveling from the cartridge chamber 80 to the interior of the pump housing. The closure 166 could be a plug structure made of a gas-permeable water barrier, which would provide a path for pressure equalization between the chamber 80 and the pump interior.

Medication Cartridge and Cartridge Interface with Drive Rod

Figure 9:
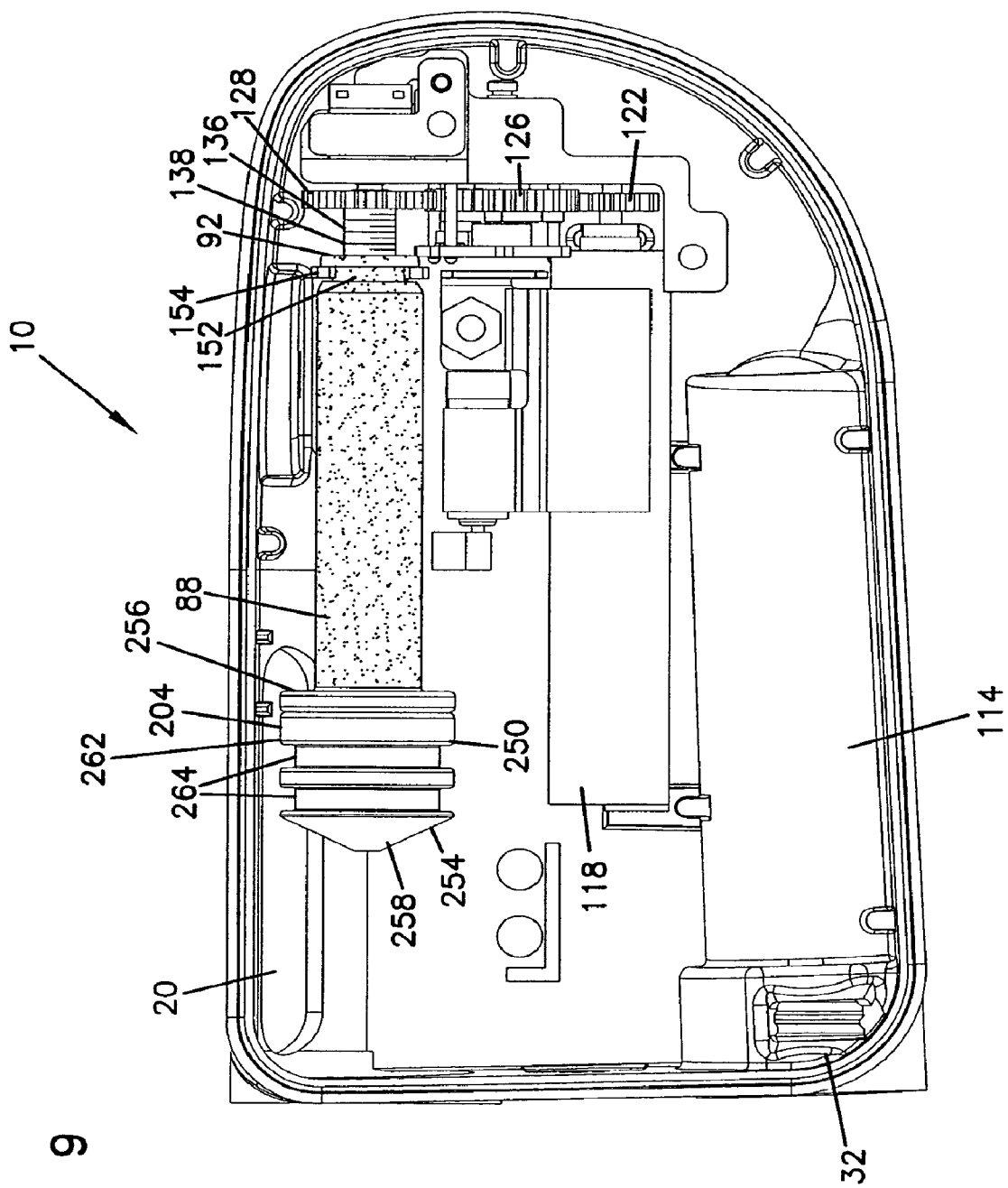
FIG. 9 is a front view of the drive assembly components within the pump housing for the pump of FIG. 1 where the cartridge chamber is not present and a plunger is attached to the end of the drive rod.
Figure 10:
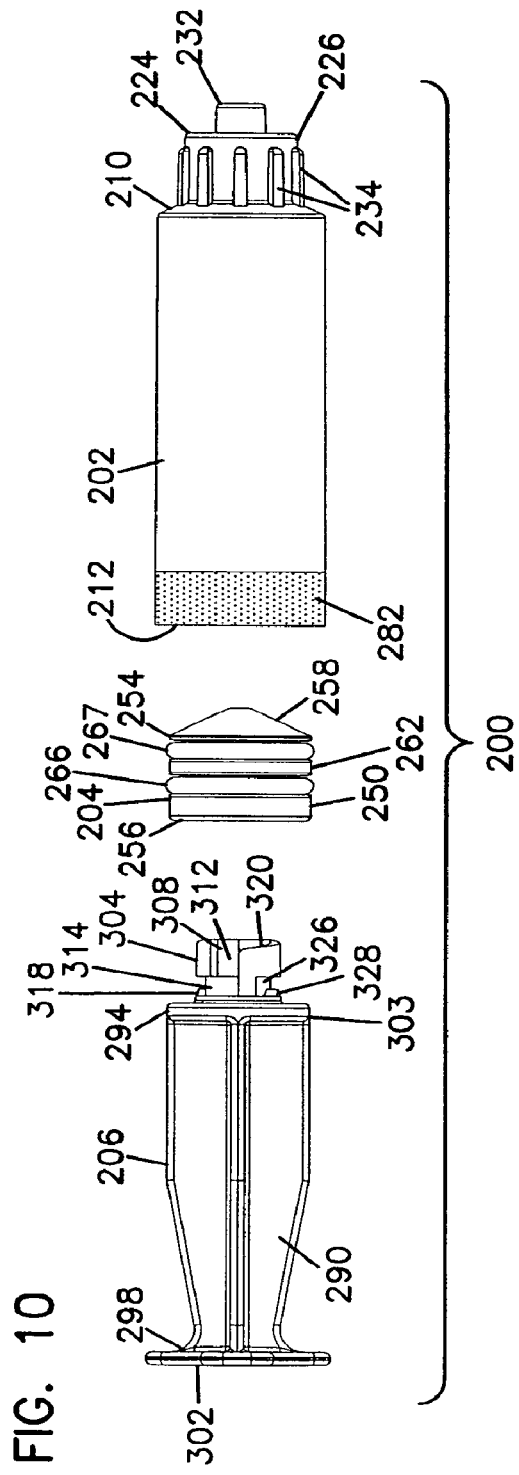
FIG. 10 is a top view of the removable cartridge rod, plunger, and cartridge barrel of a cartridge for use in a syringe pump of one embodiment of the present invention.
Figure 11:
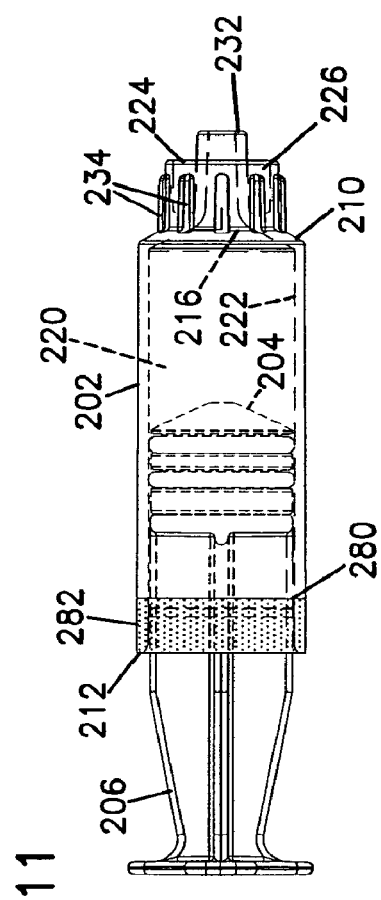
FIG. 11 is a top view showing the components of FIG. 10 where the cartridge rod is attached to the plunger and the plunger is positioned within the cartridge barrel.
Figure 12:
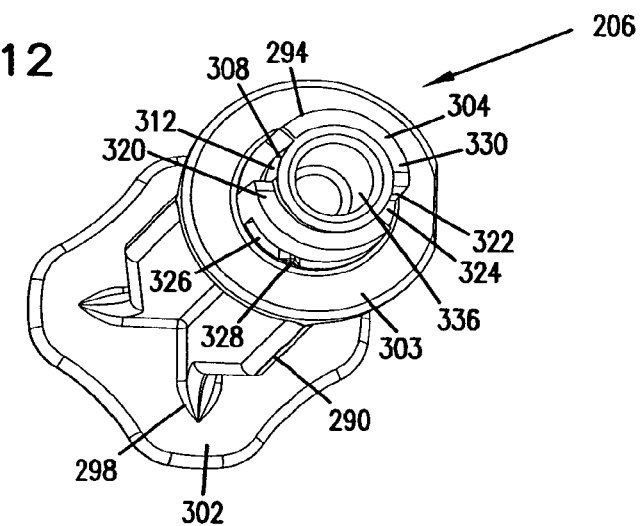
FIG. 12 is a perspective end view of the removable cartridge rod of FIG. 10.

Now referring to FIGS. 10-16, a medication cartridge is shown that may be used with the pump 10 shown in FIGS. 1-7 and 9. The medication cartridge 200 may include a cartridge barrel 202, a plunger 204 and a cartridge rod 206. The cartridge barrel 202 is cylindrically shaped and includes a closed end 210 and an open end 212. The closed end 210 defines an orifice 216 through which medication can be delivered. As seen in FIG. 11, the interior of the cylindrical cartridge barrel 202 defines a medication reservoir 220 bounded by a barrel interior wall 222. The cartridge barrel 202 may also include a cylinder 224 protruding from the closed end 210. The cylinder 224 includes an exterior wall face 226 and an interior wall face 228 shown in FIG. 15. Now referring to FIGS. 10, 11 and 15, the protruding end cylinder 224 surrounds a protruding tip 232. The tip 232 protrudes beyond the cylinder 224 and is in fluid communication with the orifice 216 of the cartridge barrel. On the exterior wall 226 of the end cylinder 224, axial guides 234 are defined. The axial guides 234 may be ridges molded into the structure of the protruding cylinder 224. Alternatively, the axial guides may be depressions or grooves molded into the cylinder 224. The axial guides 234 interact with the pump cap 16, as will be further described. Thread structures 236 are defined on the interior wall 228 of the protruding cylinder 224. The thread structures 236 are useful for securing an administration set 50, as illustrated in FIG. 3, to the medication cartridge 200.

In a preferred embodiment, the outer diameter of the cartridge barrel is about a half inch, or about 540 thousandths of an inch, while the inner diameter of the cartridge barrel is about 475 thousandths of an inch. The entire cylindrical barrel including the protruding cylinder and tip may preferably be about 3 inches or less, more preferably about 2 inches or less. Preferably, the maximum travel distance of the plunger from the fill line to the closed end is about an inch or less.

Figure 14:
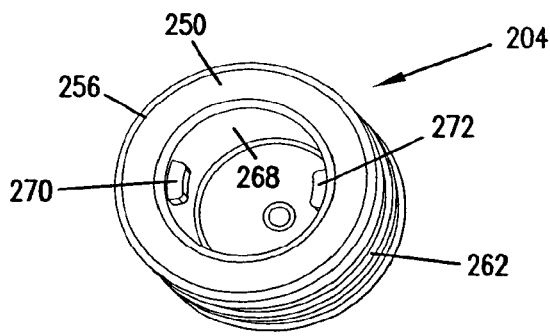
FIG. 14 is a rear perspective view of the plunger of FIG. 10.

Now referring to FIGS. 9, 10, and 14, the plunger 204 includes a cylindrical wall 250, a closed end 254, an open end 256, and a conical face 258 at the closed end 254. The cylindrical plunger wall 250 includes an exterior wall face 262 defining grooves 264 (FIG. 9) into which O-rings 266, 267 (FIG. 10) are seated. The O-rings 266, 267, seal against the interior barrel wall 222 of the medication cartridge barrel 202. Now referring to FIG. 14, the cylindrical plunger wall 250 also includes an interior wall face 268. A first tab 270 protrudes inwardly from the interior face 268 of the plunger cylinder wall 250. In a preferred embodiment of the plunger of the present invention, a second tab 272 also protrudes from the interior wall 268 of the plunger. Preferably, the first and second tabs are positioned opposite each other on the cylindrical interior wall face 268.

The tabs 270, 272 are designed for mating with another structure that is used to move the plunger, such as a removable cartridge rod 206 for filling or a drive rod 88 of a pump 10 for pumping. Many different numbers and configurations of tabs, or other protruding structures, may be provided on the interior wall 268 of the plunger 204 to allow for mating with another structure. For example, one, two, three, four, five, six or more tabs may be provided on the interior wall 268. Two or more tabs are preferred to one tab, and it is preferred that the tabs are evenly spaced around the interior wall face 268, so that force can be evenly applied to withdraw the plunger in the cartridge. The plunger 204 is sized to be slidably received within the medication reservoir 220 of the cartridge barrel 202. The O-rings 266, 267 provide a sealing engagement with the barrel interior wall 222 so that the plunger can be used to push medication out of the medication reservoir 220.

Figure 15:
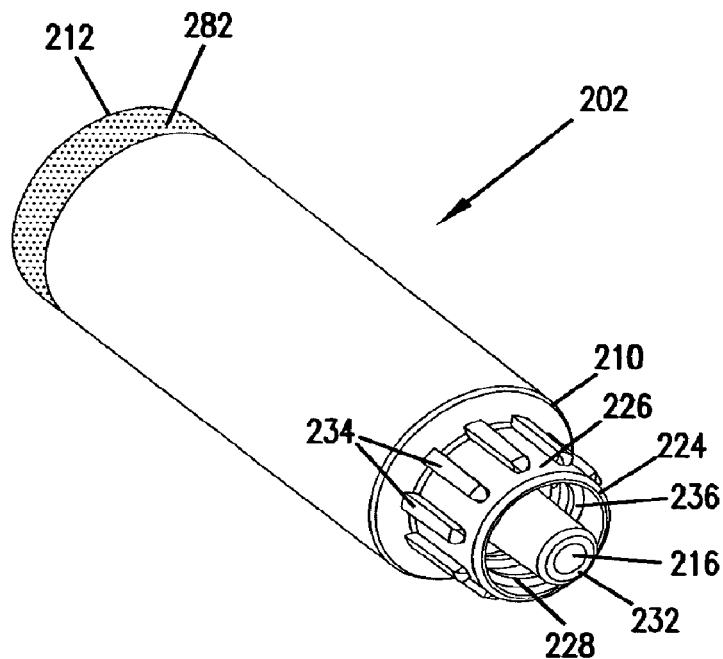
FIG. 15 is a front end perspective view of the cartridge barrel of FIG. 10.
Figure 16:
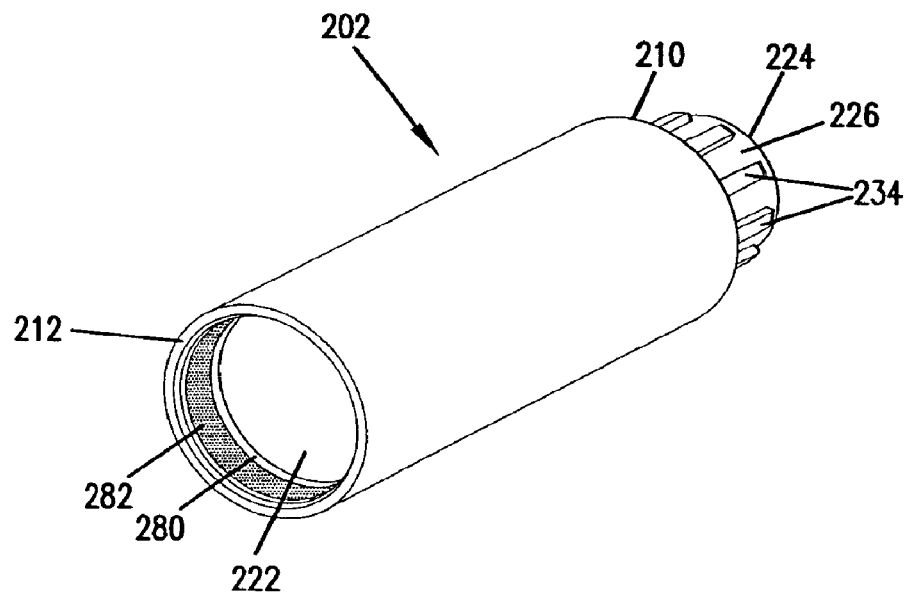
FIG. 16 is a back end perspective view of the cartridge barrel of FIG. 10.
Figure 17:
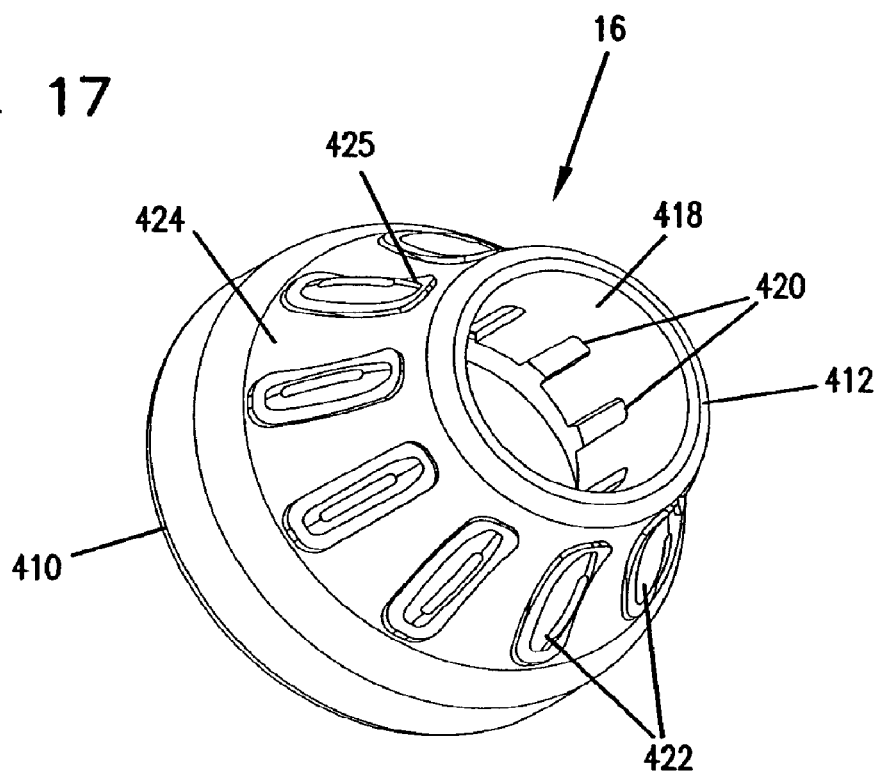
FIG. 17 is a top perspective view of a pump cap according to one embodiment of the present invention.
Figure 18:
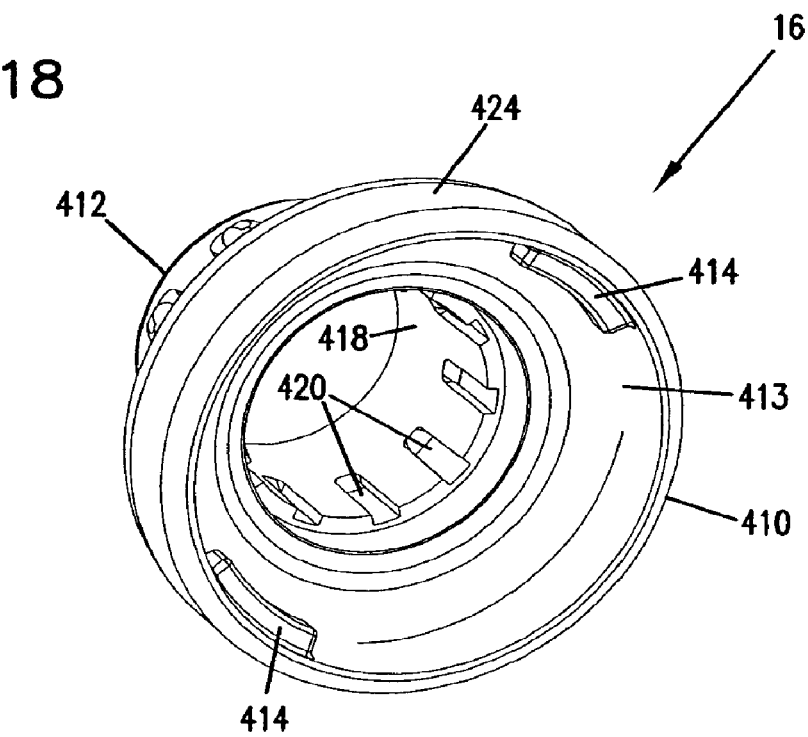
FIG. 18 is a bottom perspective view of the pump cap of FIG. 17.
Figure 19:
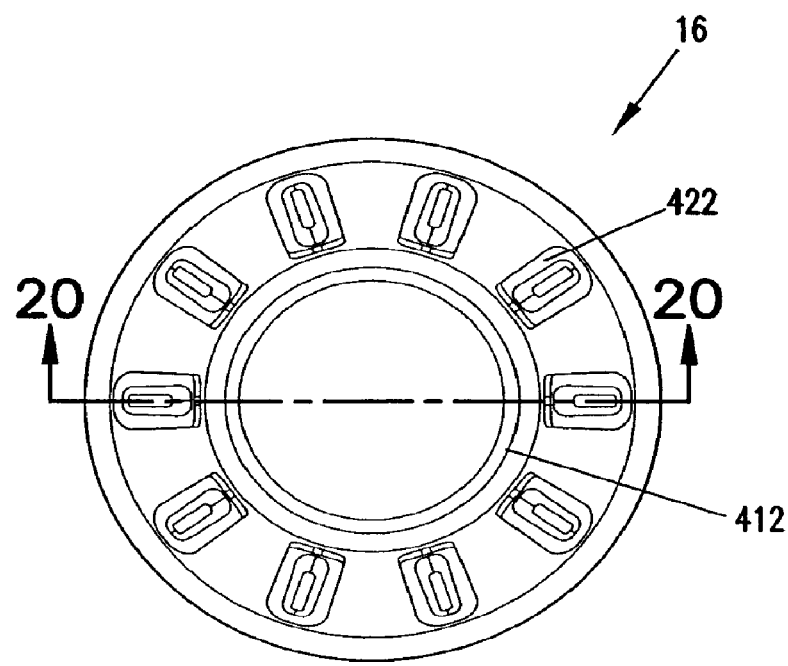
FIG. 19 is a top view of the pump cap of FIG. 17.

Now referring to FIG. 16, the cartridge barrel 202 may include a fill line ridge 280 projecting from the interior barrel wall 222 near the open end 212. The fill line ridge 280 provides a tactile indication of the fully retracted position for the plunger 204. As a user pulls the plunger away from the closed end 210, for example when filling the medication reservoir 220 with fluid, the rearmost O-ring 266 will come into contact with the fill line ridge 280. When the O-ring 266 contacts the fill line ridge 280, an increased force will be necessary to further withdraw the plunger past the fill line ridge 280. As the O-ring 266 passes over the fill line ridge 280, a tactile bump will be felt by the user. This indicates that the plunger should not be withdrawn further in the medication reservoir. Optionally, the portion 282 of the cylindrical barrel 202 that extends from the ridge fill line 280 to the open end 212 may be shaded or textured. This shading or texturing may provide the user with a visual indication of the fill line. In addition, the shaded or textured portion 282 may be useful in conjunction with a cartridge sensor that will be further discussed herein. Shading or texturing may be provided on either the interior or the exterior of the barrel 202 at the shaded or textured portion 282. FIGS. 10-11 and 15 illustrate a shaded portion 282 on the exterior surface of the barrel. FIG. 16 illustrates a shaded portion 282 on an interior surface of the barrel. Alternatively, the shading or texturing could be incorporated into the material of the barrel 202.

The cartridge fill rod 206 shown in FIGS. 10-13 may be removably coupled to the plunger 204 and may be used to move the plunger 204 axially within the cartridge barrel 202. The cartridge fill rod 206 may be especially useful for filling the medication cartridge before inserting it into a pump. The cartridge fill rod 206 may be attached to the plunger 204 and then used to pull the plunger back in the medication reservoir, thereby drawing in fluid. Then, the cartridge fill rod 206 may be detached from the plunger 204 and the cartridge barrel 202 and plunger 204 may be inserted into a chamber of a pump.

The cartridge fill rod 206 includes a shaft 290 extending between an interface end 294 and a handle end 298. A handle flange 302 at the handle end 298 is useful for grasping and pulling or pushing the cartridge fill rod 206. The cartridge fill rod may also include an interface flange 303 at the interface end 294. An interface cylinder 304 may extend from the interface end 294 of the fill rod 206. The interface cylinder defines a first channel 308 for receiving and retaining a tab of the plunger 204. The first channel 308 may include two portions for receiving and retaining the portion of a plunger. The first channel 308 may include a first axial portion 312 that is disposed parallel to an axis of the cartridge fill rod 206. The first channel 308 may also include a first locking portion 314 that is disposed in a circumferential direction around the interface cylinder 304. Preferably, the junction of the first locking portion and the first axial portion forms a right angle. A portion of a plunger, such as a tab 270, is first received in an axial portion 308 of the channel 312 as the fill rod is moved axially toward the plunger. Then, the cartridge rod 206 is rotated so that the tab travels along a circumferential locking portion 314 of the channel 308. Preferably, within the locking portion 314 of the first channel 308, a ridge 318 is defined. The cartridge rod 206 is rotated so that the tab passes over the ridge 318 and is thereby more securely retained within the first channel 308. The interface cylinder 304 may also include a ramp portion 320 associated with and adjacent to the first channel 304 for guiding a portion of the plunger into the first channel 308.

Figure 13:
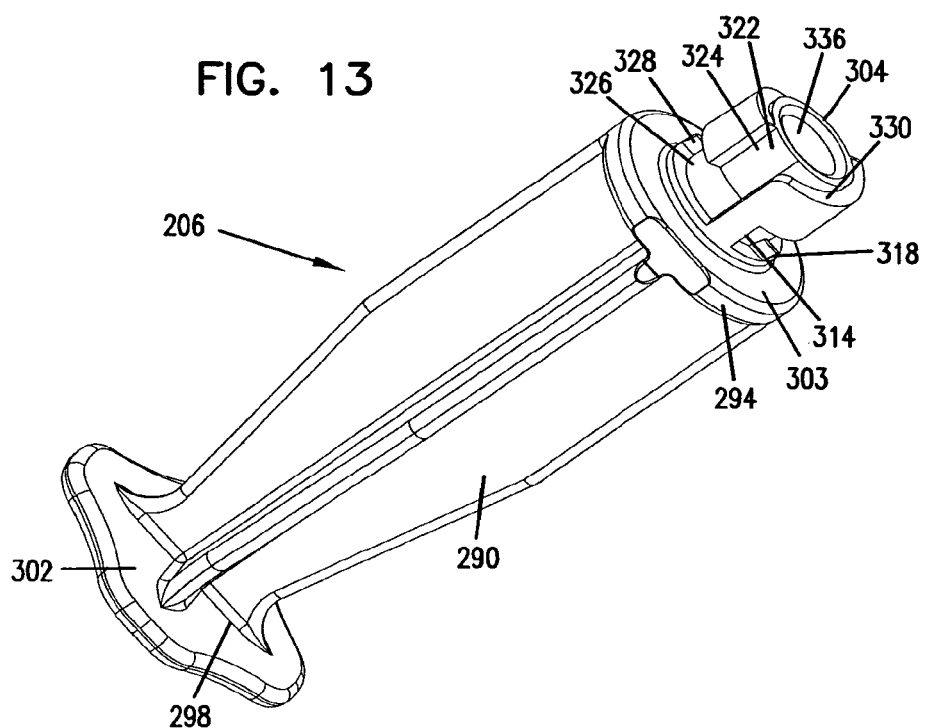
FIG. 13 is a top perspective view of the removable cartridge rod of FIG. 10.

As best seen in FIG. 13, preferably, the interface cylinder 304 also defines a second channel 322 for receiving a second portion of a plunger, such as a tab 272. The second channel 322 may include a second axial portion 324 disposed parallel to an axis of the cartridge rod 206. The second channel 322 may also include a second locking portion 326 disposed in a circumferential direction around the interface cylinder. The locking portion 326 may also include a ridge 328 over which the tab 272 may be pushed as it is rotated into the locking portion 326 of the second channel 322. Preferably, the axial and locking portions of the second channel also form a right angle. A second ramp portion 330 may be associated with the second channel 322 to guide a portion of the plunger into the second channel 322. The interface cylinder 304 of the fill rod could also include additional channels for receiving additional portions of a plunger.

The ridges 318 and 328 within the locking portions of the channels 312 and 322 may be sized so that they will contact the tabs of the plunger and configured so that they deform after the tabs of the plungers pass over them. This deformation allows the tab to move farther into the locking portion of the channel and provides the user with a tactile indication that the tabs are positioned in the locking portions of the channels. The interface cylinder 304 may include a hollow portion 336 at its interface end 294, seen in FIGS. 12-13, which is useful in facilitating the molding process if the fill rod is molded.

Cartridge Interface on Pump

Figure 8:
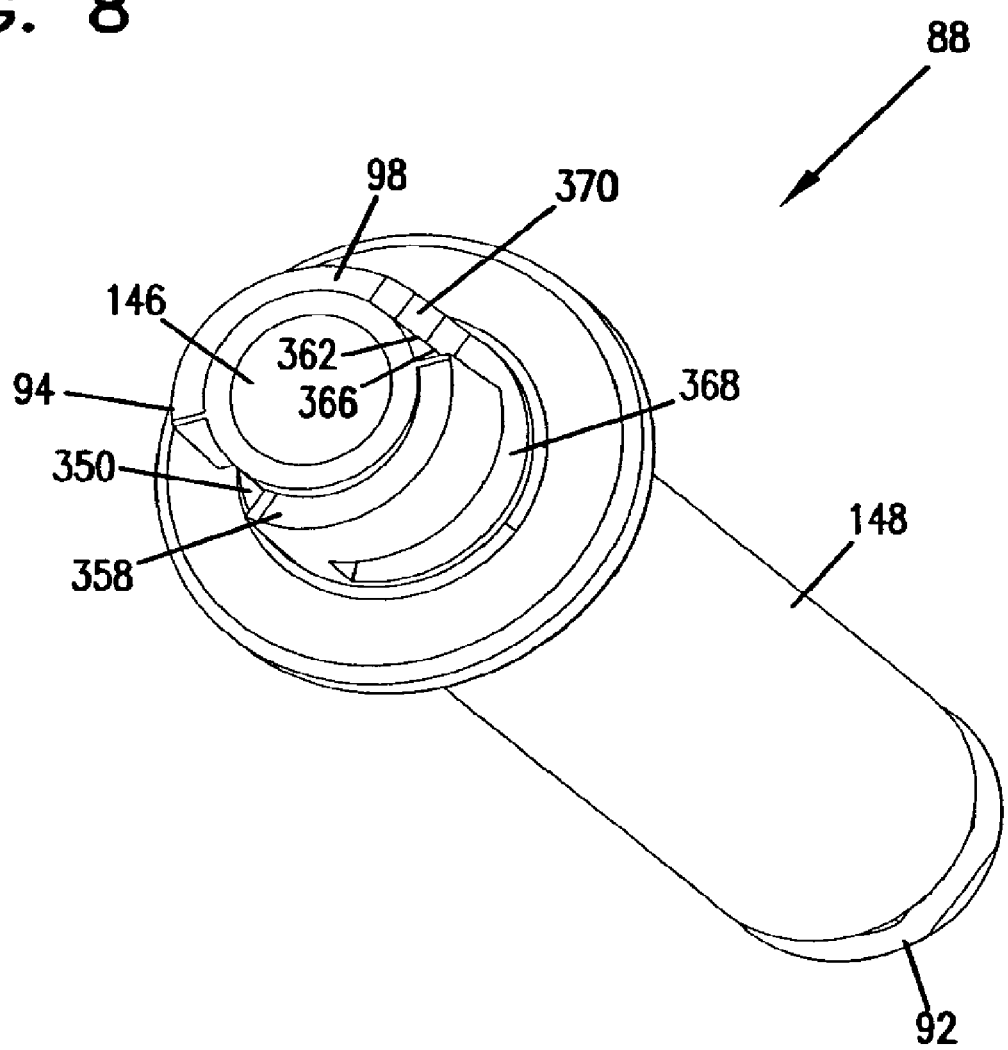
FIG. 8 is a front, right view of a drive rod of the pump of FIG. 1.

Now referring to FIGS. 4 and 8, the interface cylinder 98 of the drive rod 88 includes a structure for coupling the drive rod 88 to a plunger of a medication cartridge, such as the plunger 204 shown in FIGS. 9, 10-11 and 14. The interface cylinder 98 of the drive rod 88 may include a first channel 350 for receiving a tab of the plunger. The channel may include a first axial portion 354 extending from the second end 94 of the drive rod in a direction parallel to the axis of the drive rod. The first channel 350 may also include a first locking portion 356 extending circumferentially around the surface of the interface cylinder 98. The first channel 350 may also have a first ramp 358 associated with it to guide a tab into the first channel. The interface cylinder 98 may also include a second channel 362 opposite from the first channel on the interface cylinder 98. The second channel 362 may also include a second axial portion 366 that extends in a direction parallel to an axis of the drive rod. The second channel 362 may also include a second locking portion 368 extending circumferentially around the interface cylinder 98. The second channel 362 may also include a ramp portion 370 for guiding a tab into the second channel 362, similar to the ramp 358 associated with the first channel. The interface cylinder 98 could also include third, fourth or additional channels for receiving a portion of the plunger.

When a medication cartridge is loaded into the cartridge chamber 80, the user first removes the cartridge rod 206 from the medication cartridge 200. Then, the user inserts the medication cartridge 200 axially into the cartridge chamber 80 through the cartridge opening 28. The medication cartridge 200 is inserted axially until the plunger comes into contact with the interface cylinder 98 of the drive rod 88. If the tabs 270, 272 of the plunger 204 are aligned with the channels of the interface cylinder when the medication cartridge 200 is inserted, then the tabs will be received in the axial portions 354, 366 of the channels 350, 362 as the cartridge is further axially inserted into the cartridge chamber 80. If the tabs of the plunger 204 are not aligned with the channels of the interface cylinder when the plunger contacts the interface cylinder, the tabs will be guided into the axial portions 354, 362 of the channels 350, 352 by the ramps 358, 370 as the medication cartridge 200 is rotated. If the pump is positioned with the cartridge chamber opening facing upward, then the cartridge is dropped into the chamber, and possibly with some rotation of the cartridge, the tabs 270, 272 drop into the axial portions 354, 362 of the channels 350, 362 on the interface cylinder 98 of the drive rod 88. Once the tabs 270, 272 are positioned at the ends of the axial portions of the channels 350, 362, the cartridge is rotated so that the tabs are positioned within the locking portions 356, 368 of the two channels. Preferably, the pump is positioned with the cartridge chamber opening 28 facing up during loading so that the action of gravity may be used to help engage the tabs of the plunger with the channels on the interface cylinder 98.

Pump Cap

After the medication cartridge is inserted into the cartridge chamber 80, the pump cap 16 may be reattached to the cartridge chamber opening 28. The pump cap 16 is illustrated in FIGS. 1, 3, and 17-20. The pump cap includes a pump or attachment end 410 closest to the pump and a delivery end 412. At the pump end 410 of the pump cap 16, an interior cylindrical surface 413 is defined. Protruding from the interior cylindrical surface at the attachment end are two opposing tabs 414. These tabs are used to attach the pump cap to a mating structure 416 at the cartridge chamber opening 28, shown in FIGS. 4-5. In FIG. 1, the pump cap 16 is shown attached to the pump housing 14. The tip 232 of the medication cartridge 200 is shown within the delivery end 412 of the pump cap.

Now referring back to FIGS. 17-20, another interior cylindrical surface 418 is defined at the delivery end 412 of the pump cap 16. Axial guides 420 are defined in the interior cylindrical surface 418 at the delivery end 412 of the pump cap 16. These axial guides may interact with axial guides 234 at the closed end 210 of the cartridge barrel 202. In one embodiment, the axial guides 234 on the cartridge barrel are protruding ridges while the axial guides on the interior wall 418 of the pump cap are grooves, as illustrated. However, these structures could be reversed so that grooves would be defined on the protruding cylinder 224 of the cartridge barrel 202 and protruding ribs would be defined on the interior surface 418 of the pump cap 16. Alternatively, cooperating ridges may be formed on both the pump cap and the cartridge barrel end. The cooperating guides 234, 420 help ensure that the drive rod of the pump is securely attached to the plunger. When the pump cap 16 is rotated into attachment with the cartridge chamber opening 28, the axial guides 420 on the pump cap cooperate with the axial guides 234 on the medication cartridge to rotate the medication cartridge and plunger in a direction to secure the tabs of the plunger within the channels of the interface cylinder.

If the plunger is already attached to the drive rod when the pump cap is rotated onto the pump cap opening, then the interacting guides 234 and 420 will cause the cartridge barrel to rotate around the plunger, while the plunger remains fixed to the drive rod. Once the drive rod is attached to the plunger, the rotation of the pump cap does not cause any axial movement of the plunger relative to the barrel, so no fluid is caused to be ejected from the barrel and no air is drawn into the barrel.

When the pump cap 16 is removed from the pump housing 14, the cooperating guides 234, 420 cause the medication cartridge 200 to rotate also. This rotation moves the tabs out of the locking portion of the channels on the drive rod interface structure 98, thereby facilitating removal of the medication cartridge from the cartridge chamber.

Figure 20:
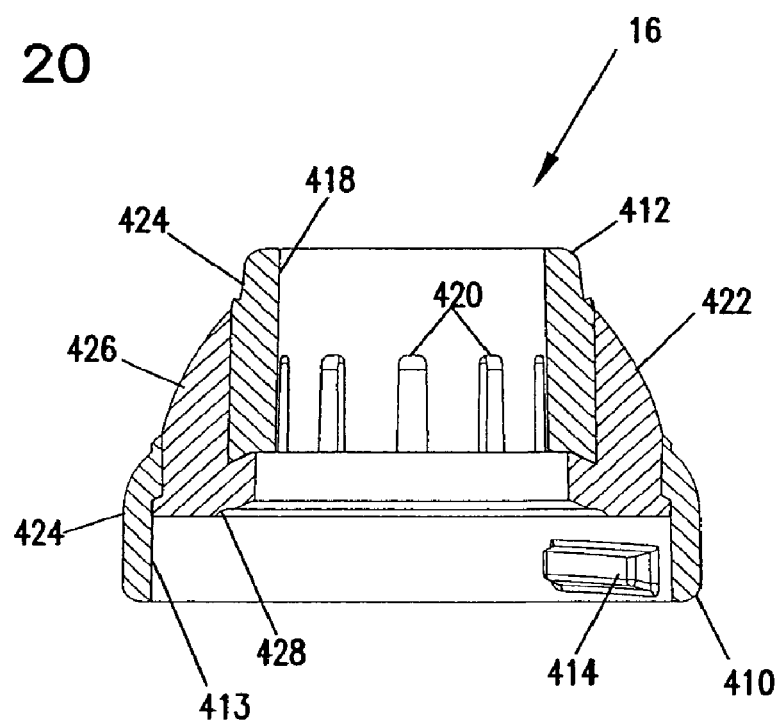
FIG. 20 is a cross-sectional view of the pump cap of FIG. 17 taken along line 20-20 of FIG. 19.

On the exterior surface of the pump cap 16, gripping members 422 are defined. The gripping members 422 may provide the user with structure to grasp when removing or attaching the pump cap. The gripping structures 422 may also interact with a cap cover as further described herein. In a preferred embodiment, the gripping structures 422 are made of an elastomeric material. The pump cap 16 may include two materials such as a molded polymeric material and a molded elastomeric material. The exterior wall surface extending between the pump end 410 and the delivery end 412 is made of the molded polymeric material and defines openings 425 that surround the gripping structures 422. The molded polymeric portion 424 is shown in FIG. 20. An elastomeric portion 426 may be formed within the polymeric portion 424, so that the elastomeric gripping structures 422 protrude from the openings 425. As seen in the cross-sectional view of FIG. 20, the polymeric portions 424 surround the elastomeric portions 426. A lower portion of the elastomeric portion 426 may form a seal area 428 for interacting with the cartridge chamber opening 28 and with the closed end 210 of the medication cartridge 202.

Visual Indicator of Drive Rod Attachment to Cartridge

Now referring to FIG. 4, at least a portion of the interface cylinder 98 may include a visual indicator to assist the user with confirming that the interface cylinder is properly attached to the plunger 204. A viewing window 20, shown in FIG. 1, provides a view into the cartridge chamber 80. Preferably, the cartridge chamber 80 is made of a fairly transparent material so that a user can view the interface cylinder 98 within the chamber. When the plunger is not attached to the interface cylinder, the visual indicator on the interface cylinder 98 will be visible to the user through the window 20. However, when the interface cylinder 98 is properly attached to the plunger 204, the visual indicator will be hidden within the wall 250 of the plunger 204. FIG. 9 shows a view of the pump drive assembly where the plunger 204 is properly attached to the drive rod 88. As a result, the interface cylinder 98 is not visible. In FIG. 9, the cartridge chamber 80 is not shown so that the attachment to the plunger may be more clearly illustrated.

The visual indicator on the interface cylinder may take a variety of forms. For example, a portion of or the entire surface of the interface cylinder 98 may include a dark color, a pattern, a bright color, or other readily observable markings. In the embodiment shown in FIG. 4, the entire drive rod is a dark color, such as brown or black. Alternatively, at least the end of the drive rod may be bright pink. In another alternative, a black and white pattern is present on the interface cylinder.

Cartridge Sensor

Figure 21:
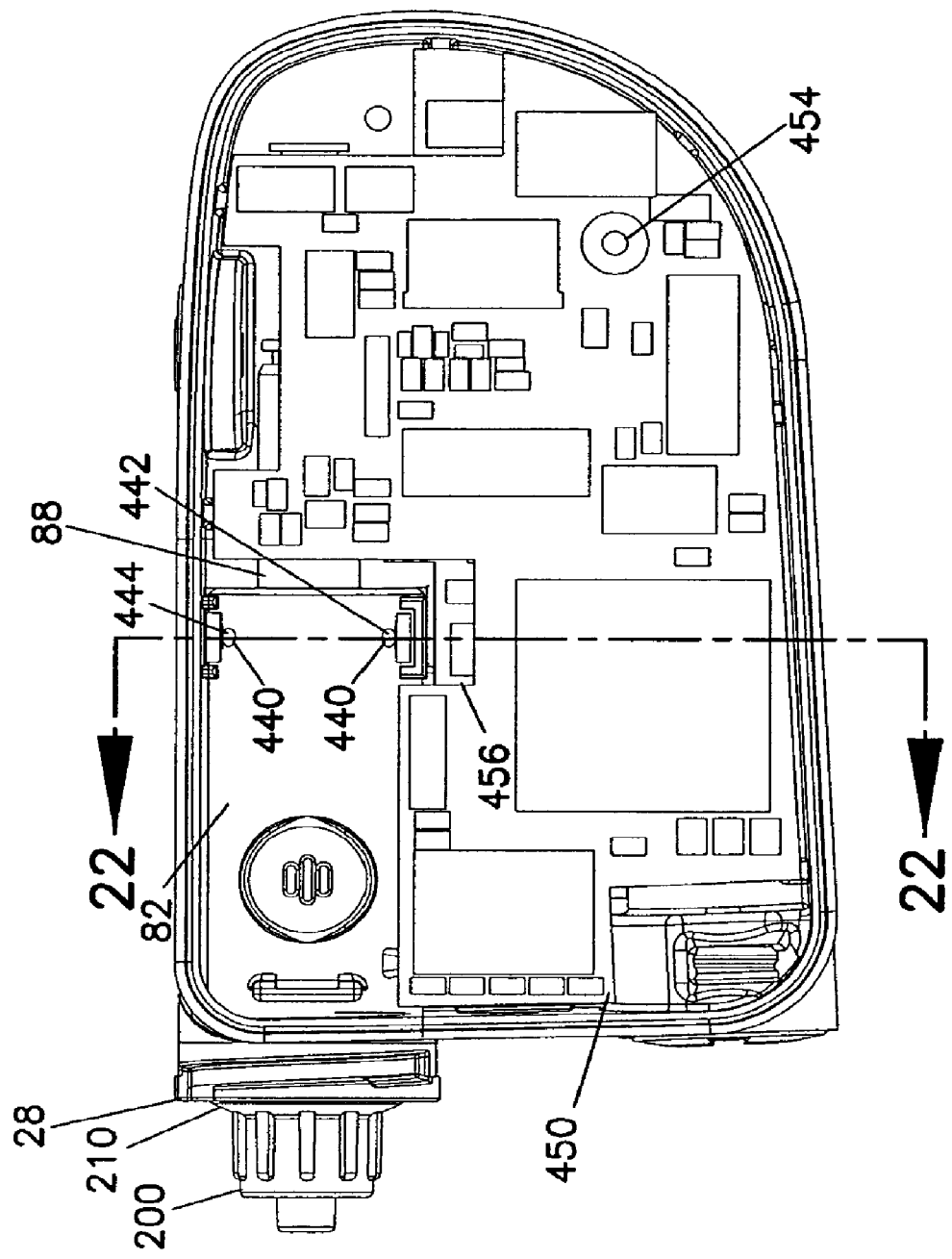
FIG. 21 is a front view of the pump of FIG. 1 where a medication cartridge is loaded in the cartridge chamber.
Figure 22:
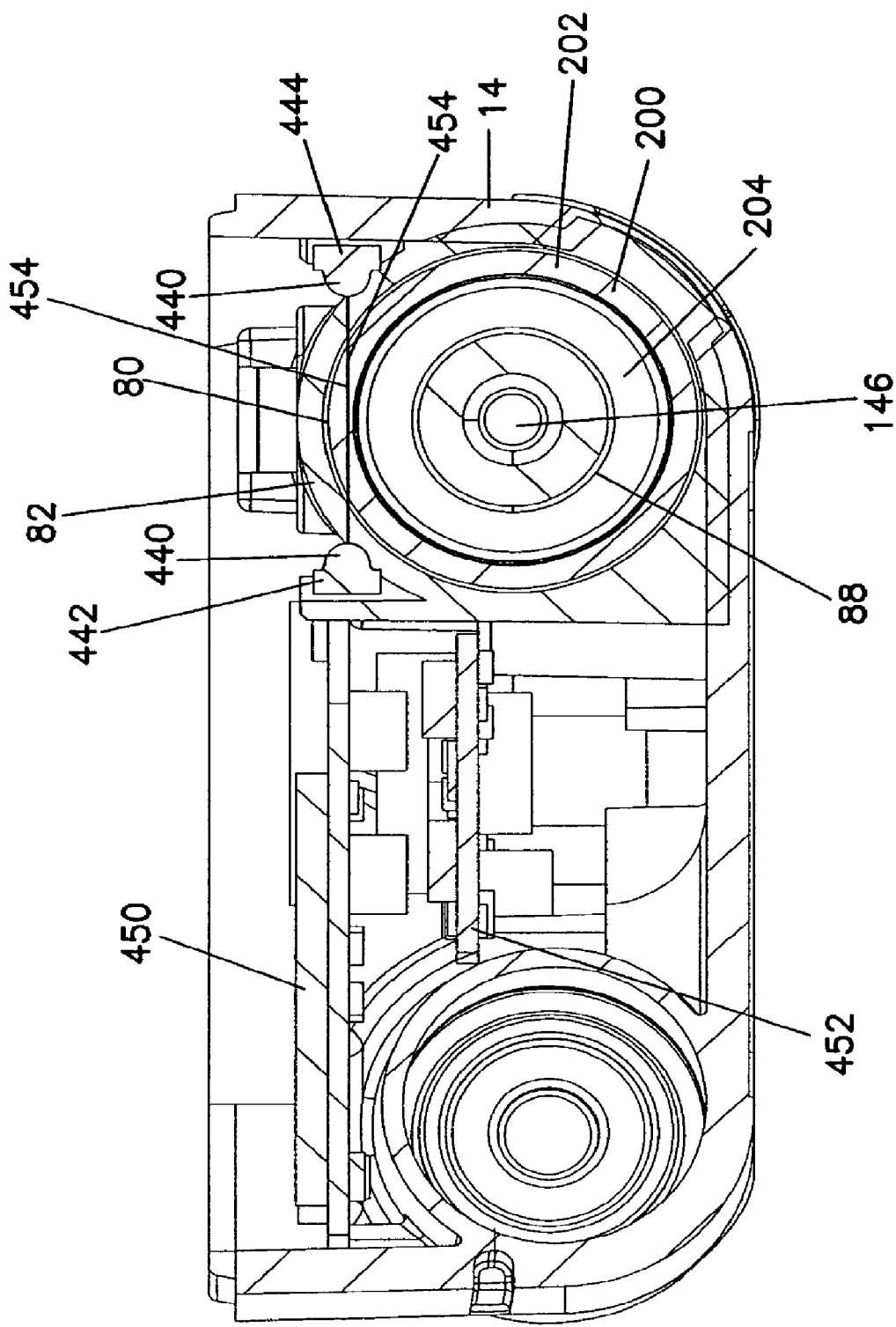
FIG. 22 is a cross-sectional view of the pump of FIG. 21 along line 22-22 of FIG. 21.

A pump according to the present invention may be provided with a cartridge sensor 440 configured to confirm whether or not a cartridge is present in the cartridge chamber 80. In one embodiment of the invention, a cartridge sensor assembly 440 includes a light emitter 442 located opposite a light detector 444 across the cartridge chamber 80 at the closed end 102 of the cartridge chamber 80, as shown in FIGS. 4-5, 21-22 and 29. FIGS. 21 and 22 illustrate a pump housing 14 including the drive assembly components, circuit boards 450 and 452, and a medication cartridge 200 positioned within the cartridge chamber 80. The closed end 210 of the medication cartridge 200 protrudes from the chamber cartridge opening 28 in FIG. 21. FIG. 22 is a cross-sectional view along line 22-22 of FIG. 21, through the emitter 442 and the detector 444. A line 454 connecting the emitter 442 with the detector 444 draws a chord across a top portion of the cylindrical barrel 202 within the cartridge chamber 80. The chord 454 is provided in FIG. 22 for illustration purposes only, to show the path of light between the emitter 442 and the detector 444, and is not part of the pump. The chord 454 does not pass through the drive rod 88 or the plunger 204.

The sensor 440 is preferably positioned on the outside of the cartridge chamber 80. The detector 444 detects light from the emitter 442 through the partially transparent cartridge chamber wall when the cartridge chamber is empty. By positioning the sensor 440 outside of the cartridge chamber wall 82, the sensor 440 is less likely to be in contact with fluid or dirt which could affect its operation. As shown in FIG. 2, a support 445 and a detent 446 are used to mount and position emitter 442. Similar structures can be provided to mount the detector 444.

When a medication cartridge 200 is present in the cartridge chamber 80, the open end 212 of the cylindrical barrel 202 will be adjacent to the closed end 102 of the cartridge chamber 80. Accordingly, the end of the cartridge barrel 202 will interrupt the light transmission between the emitter 442 and the detector 444. The sensor 440 may therefore be used to indicate whether a cartridge is present in the cartridge chamber 80.

Typically, a barrel 202 of a medication cartridge 200 is at least partially transparent so that the level of fluid within the reservoir 220 can be viewed. However, at least an end portion of the barrel is preferably sufficiently opaque that it interrupts light transmission between the two sensors. An end portion 282 of the cartridge barrel 202 may be textured or shaded in order to ensure that light transmission is interrupted between the emitter 442 and the detector 444. The texturing or shading on the cylindrical barrel 202 of the medication cartridge may be provided on an inside surface of the barrel 202, an exterior surface of the barrel 202, or throughout the material of the barrel wall. It is also possible for the sensor 440 to be able to detect the cartridge barrel 202 without any texturing or shading present at the end of the cartridge barrel. Preferably, most of the barrel is sufficiently transparent to allow viewing of the medication level, while at least the end portion of the barrel is sufficiently opaque to interrupt light transmission between the emitter 442 and the detector 444.

Idler Gear Sensor

Figure 23:
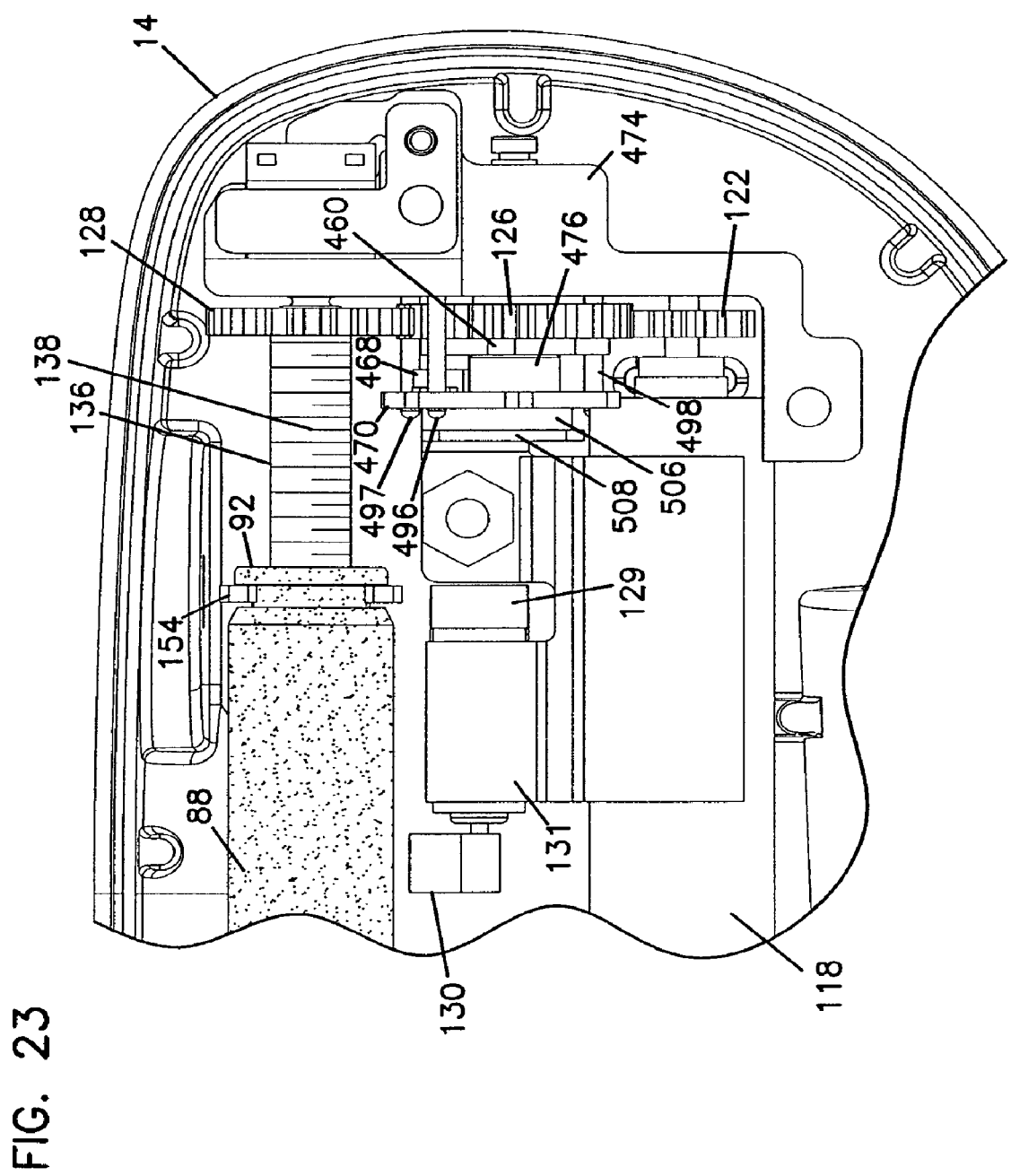
FIG. 23 is an enlarged view of the pump components of FIG. 1 within the pump housing.
Figure 24:
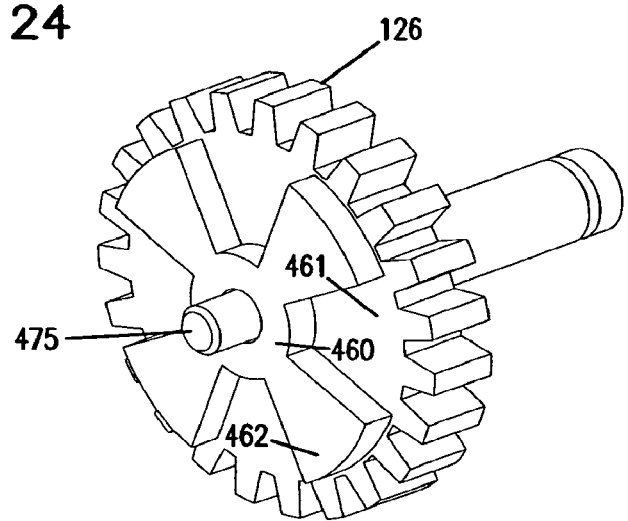
FIG. 24 is a front perspective view of an idler gear having a magnetic flag according to one embodiment of the present invention.
Figure 25:
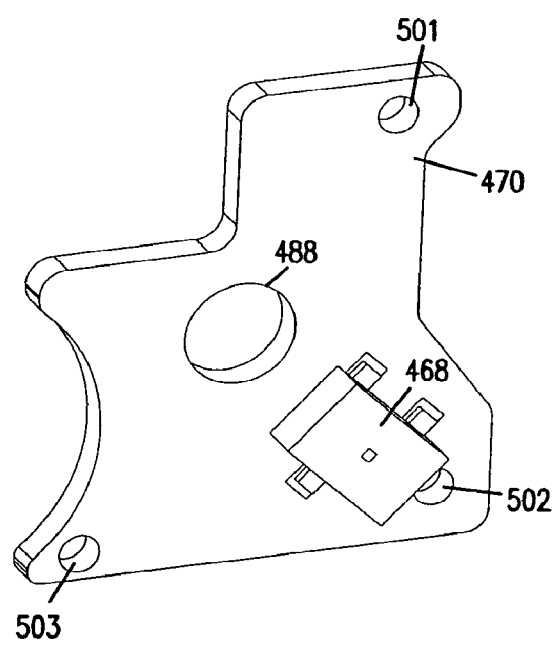
FIG. 25 is a front perspective view of an idler gear circuit board according to one embodiment of the present invention.

The idler gear 126 is intermediate between the motor gear 122 and the drive gear 128 as shown in FIG. 23. According to one embodiment of the present invention, a sensor may be provided to determine whether or not a gear in the pump, such as the idler gear 126, is rotating as a confirmation that the pump is operating normally. Components of an idler gear sensor are described with respect to FIGS. 23-29. A magnetic flag 460 may be provided on a front face 461 of the idler gear 126 as shown in FIG. 24. The magnetic flag 460 may include a plurality of legs 462 extending from the center of the idler gear to near an outer perimeter of the idler gear. To determine whether or not the idler gear 126 is rotating, a magnetic sensor 468 may be provided within the pump interior near the magnetic flag 460, as shown in FIG. 23. The magnetic sensor 468, for example, a Hall Effect sensor, can determine the magnetic field at a point near the idler gear 126. Therefore, as the magnetic field at a point near the idler gear fluctuates because of the rotation of the magnetic flag 460, the sensor 468 measures the magnetic field.

Preferably, the sensor 468 is spaced away from a point on the idler gear that is near the outer diameter of the idler gear. In one embodiment, the magnetic sensor and magnet is configured so that the sensor detects a magnetic field when one of the legs 462 is directly in front of the sensor and detects no field when one of the spaces between the legs 462 is directly in front of the idler gear. As the idler gear rotates, the sensor outputs information indicating the magnetic field. In this configuration, the sensor output is approximately a square wave indicating when the magnetic field is detected and when it is not detected. This information can be used by a processor to confirm that the pump is operating properly, and to signal an alarm or appropriate message if desirable. The processor may also have an input from the motor 118 indicating the number of motor cycles, or encoder counts, occurring over time. Based on the number of times a magnetic field is sensed at the magnetic sensor, the number of encoder counts, and the gear ratios, the processor can confirm that operation is normal.

The magnetic sensor 468 is preferably positioned on a circuit board 470. In order to provide accurate determinations of the magnetic field and consequently the rotation of the idler gear, the magnetic sensor 468 is maintained at a specific distance from the magnetic flag 460 on the idler gear 126. A bushing 476 may be used to provide a fixed distance between the magnetic flag 460 and the circuit board 470. The bushing, illustrated in FIGS. 23 and 26, includes a hollow cylindrical portion 477 for receiving a shaft end 475 of the idler gear 126. The hollow portion 477 is defined adjacent to a first end 482 of the bushing 476. A second end 484 of the bushing 476 is situated opposite from the first end 482. The second end 484 fits within the opening 488 in the circuit board 470. Therefore the circuit board is spaced from the magnetic flag 460 by the width W of the widest portion of the bushing 476.

Figure 28:
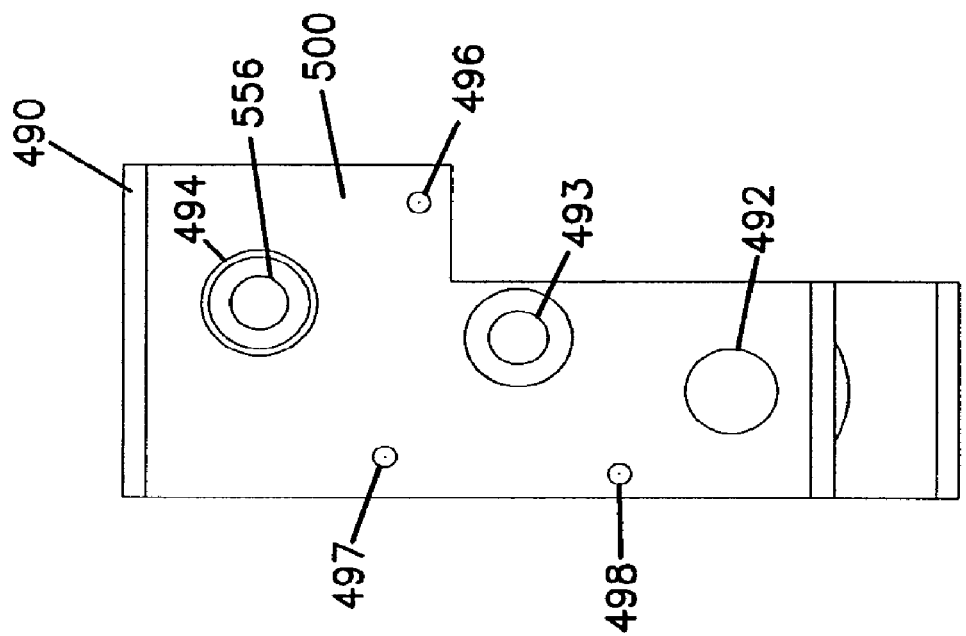
FIG. 28 is a right view of the drive assembly chassis of FIG. 27.
Figure 27:
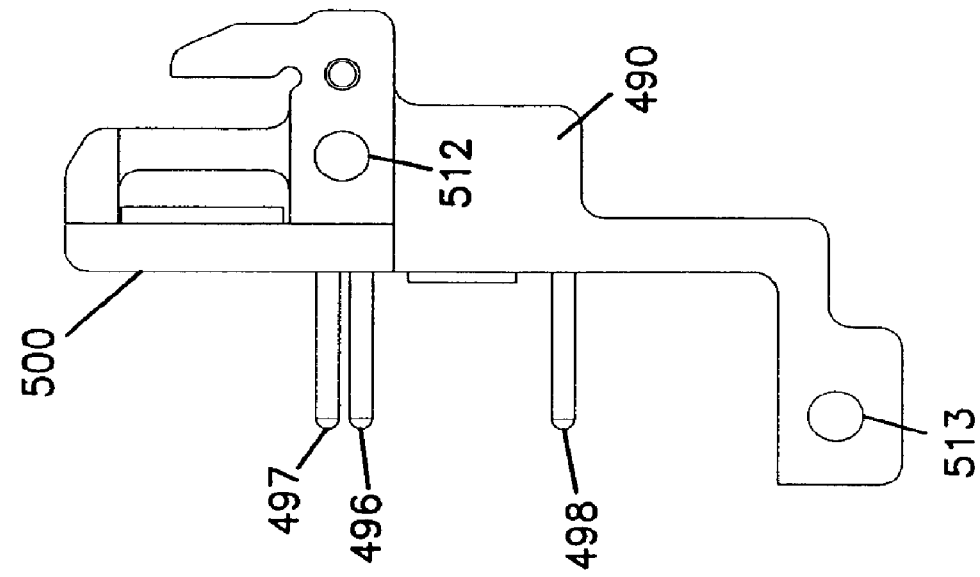
FIG. 27 is a front view of a drive assembly chassis of the present invention.

Additional stability for the circuit board 470 may be provided by a drive mechanism chassis, shown in FIGS. 23, 27 and 28, that supports the three gears of the pump. The drive mechanism chassis includes an opening 492 for a shaft of the motor gear 122, an opening 493 for a shaft of the idler gear 126, and an opening 494 for a shaft of the drive gear 128. In addition, the drive mechanism chassis 490 includes a number of pins that are used to support the circuit board 470. First pin 496, second pin 497 and third pin 498 protrude from a front surface 500 of the drive mechanism chassis 490. The pins protruding from the drive mechanism chassis 490 may be received within openings in the circuit board 470. In a preferred embodiment, a first pin 496 is received in a first hole 501 on the circuit board. The second pin 497 and the third pin 498 are received in the second hole 502 and the third hole 503, respectively, of the circuit board 470. The drive mechanism chassis 490 may be secured to the pump housing by screws through openings 512 and 513 on the chassis, corresponding to openings 515 and 516 on the rear of the pump housing, shown in FIG. 1.

In the embodiment show in FIG. 27, the pins 496, 497, and 498 have a uniform outer diameter slightly less than the diameter of the openings 501, 502, and 503 on the circuit board 470, so that the pins fit within the openings. In an alternative embodiment, the pins 496, 497, and 498 each have a smaller diameter end portion and a larger diameter base portion. The end portion of each pin fits into the openings 501, 502 and 503. The larger diameter base portion provides a hard stop against which the circuit board 470 can rest. This configuration helps provide the correct spacing between the circuit board and the drive mechanism chassis.

Additional stability may be provided to the circuit board 470 by providing a bracket 508 behind the circuit board 470. A resilient foam layer 506 may also be provided between the circuit board 470 and the bracket 508 to push the circuit board 470 toward the bushing 476.

Pressure Sensor

Now referring to FIGS. 5-6, in a preferred embodiment of a pump of the present invention, a pressure sensor 550 is also included in the pump 10. The pressure sensor 550 may be positioned behind the end 554 of the lead screw 136 that interfaces with the drive gear 128. If the drive rod 88 encounters resistance as it advances into the cartridge chamber 80, then the lead screw 136 will be pushed back toward the drive gear 128. As shown in FIG. 6, the end 554 of the lead screw 136 contacts a strain element 552 of the pressure sensor. The strain element 552 deflects as a result of pressure from the lead screw. Preferably, the pressure sensor 550 registers even very small deflections caused in the strain element 552. For example, the pressure sensor 550 could be configured to allow the strain element to deflect about 20 mils or less, more preferably 10 mils or less, and most preferably about 5 mils before sending a signal to the pump's processor.

One reason the drive rod 88 might encounter greater than normal resistance as it advances in a cartridge is an occlusion in tubing connected to a cartridge within the chamber. A blockage in a cannula inserted into a user or at the users infusion site could also be detected by the pressure sensor. Preferably, the processor connected to the pressure sensor alerts the user to a possible occlusion when the strain element deflects.

As seen in FIG. 6, a portion of the lead screw 136 near end 554 is supported by the drive chassis mechanism 490. The lead screw 136 is positioned within an opening 494 in the drive mechanism chassis 490. Within the opening 494, a Teflon support 556 surrounds the lead screw 136. The Teflon support provides a low friction interface between the lead screw 136 and its support in the drive mechanism chassis 490 so that the lead screw can more easily rotate and move axially toward the pressure sensor 550 when the drive rod encounters resistance. A top bracket 558 helps maintain the pressure sensor 550 in its proper position. The top bracket 558 includes an opening 560 that is aligned with an opening 512 on the drive mechanism chassis. Bracket opening 560, chassis opening 512 and pump housing opening 515 may receive a screw or other structure for holding the top bracket 558 and the drive mechanism chassis 490 in a stable position with respect to the pump housing 14.

In one embodiment, the pressure sensor 550 is configured to detect a negative pressure in the system that would pull the plunger and drive rod toward the open end of the cartridge chamber. A negative pressure might occur if a vacuum was drawn on the cartridge or tubing, if the medication freely flowed from the cartridge, or if the cartridge was removed from the cartridge chamber. The strain element 552 is spring-loaded so that it could deflect toward the lead screw if the drive rod was pulled toward the open end of the chamber. A deflection of the strain element toward the open end of the cartridge is communicated to the processor, and this information may cause an alarm or may be taken into account in pump operations, such as the cartridge loading process.

Pump System

Figure 30:
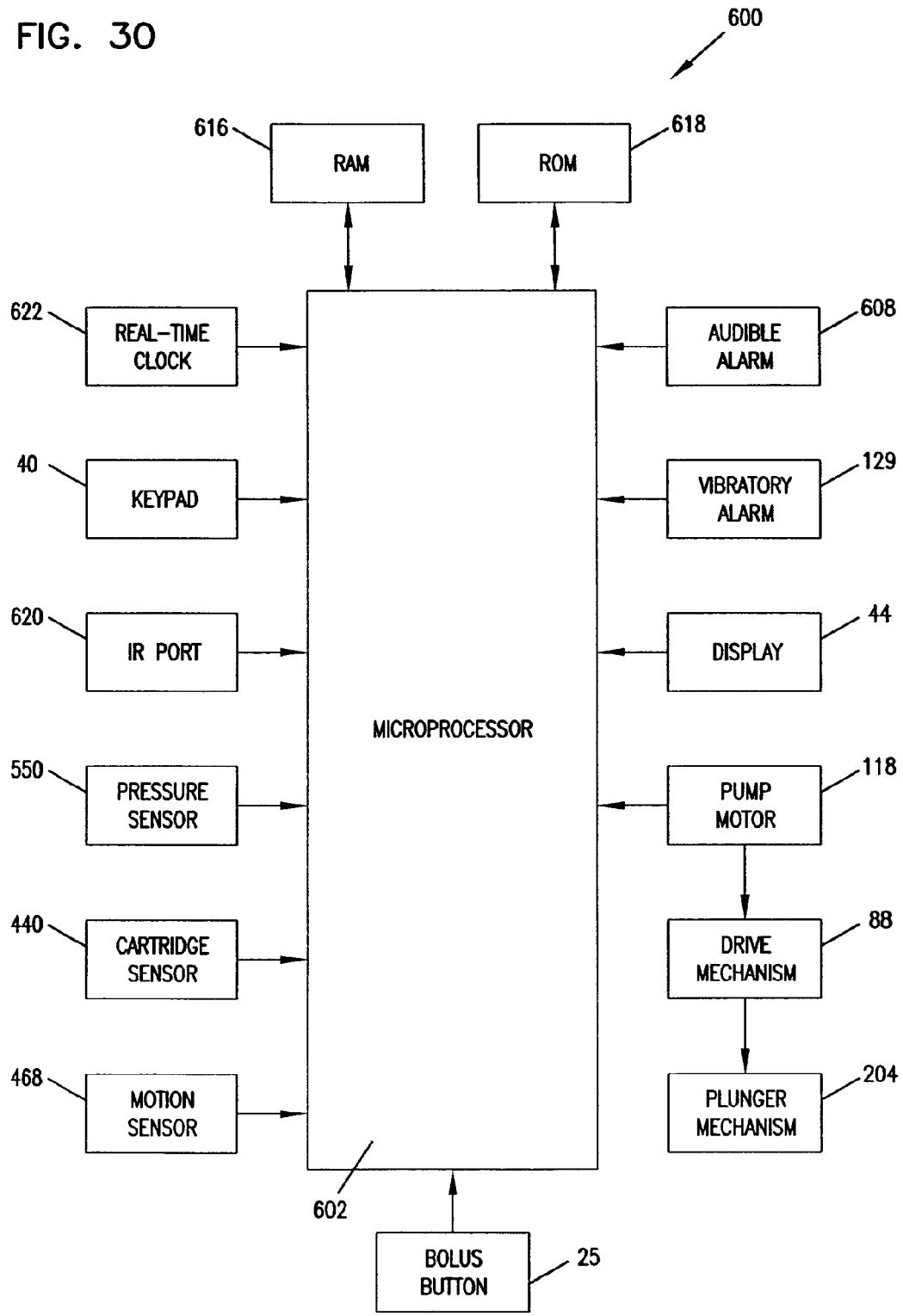
FIG. 30 is a block diagram of the components of the pump of FIG. 1.

FIG. 30 is a functional block diagram illustrating one of many possible embodiments of a medication pump, generally identified as 600. A microprocessor 602 is in electrical communication with and controls a pump motor 118, a display 44, an audio alarm 608, and a vibratory alarm 129. The pump motor 118 causes the actuation of the drive rod or drive mechanism 88 that pushes the plunger 204.

Other embodiments can use a microcomputer, or any other type of programmable circuit, in place of the microprocessor. Further possible functions of the processor and other pump components are described and illustrated in the following four commonly assigned co-pending United States patent applications, which were previously incorporated by reference: "Insulin Pump Having Missed Meal Bolus Alarm" U.S. application Ser. No. 10/087,460, now U.S. Pat. No. 6,744,350, "Programmable Medical Infusion Pump Displaying a Banner" U.S. application Ser. No. 10/087,205, "Programmable Insulin Pump" U.S. application Ser. No. 10/086,641, now U.S. Pat. No. 6,852,104 and "Programmable Medical Infusion Pump" U.S. application Ser. No. 10/087,449.

The display 44 can have many different configurations such as an LCD display. The display 44 displays various items of information that are useful to a patient or caregiver. The audio alarm 608 may be a beeper. Similar to other portable electronic devices such as a cellular telephone, the vibratory alarm 129 provides an alarm when an audible beep would be disruptive. A user can selectively enable or disable the audio 608 and vibratory 129 alarms. In one possible embodiment, however, both the audio 608 and vibratory 129 alarms cannot be disabled at the same time.

The microprocessor 602 is in electrical communication with both a random access memory (RAM) 616 and a read only memory (ROM) 618. The RAM 616 is a static RAM that stores data that can change over time such as pump settings and a historical log of events experienced by the pump 600. The ROM 618 stores code for the operating system and the application programs. The ROM 618 can be any type of programmable ROM such as an EPROM. In one possible embodiment, the RAM 616 has about 500 kilobytes of memory capacity and the ROM 618 has about 2 megabytes of memory capacity.

Figure 29:
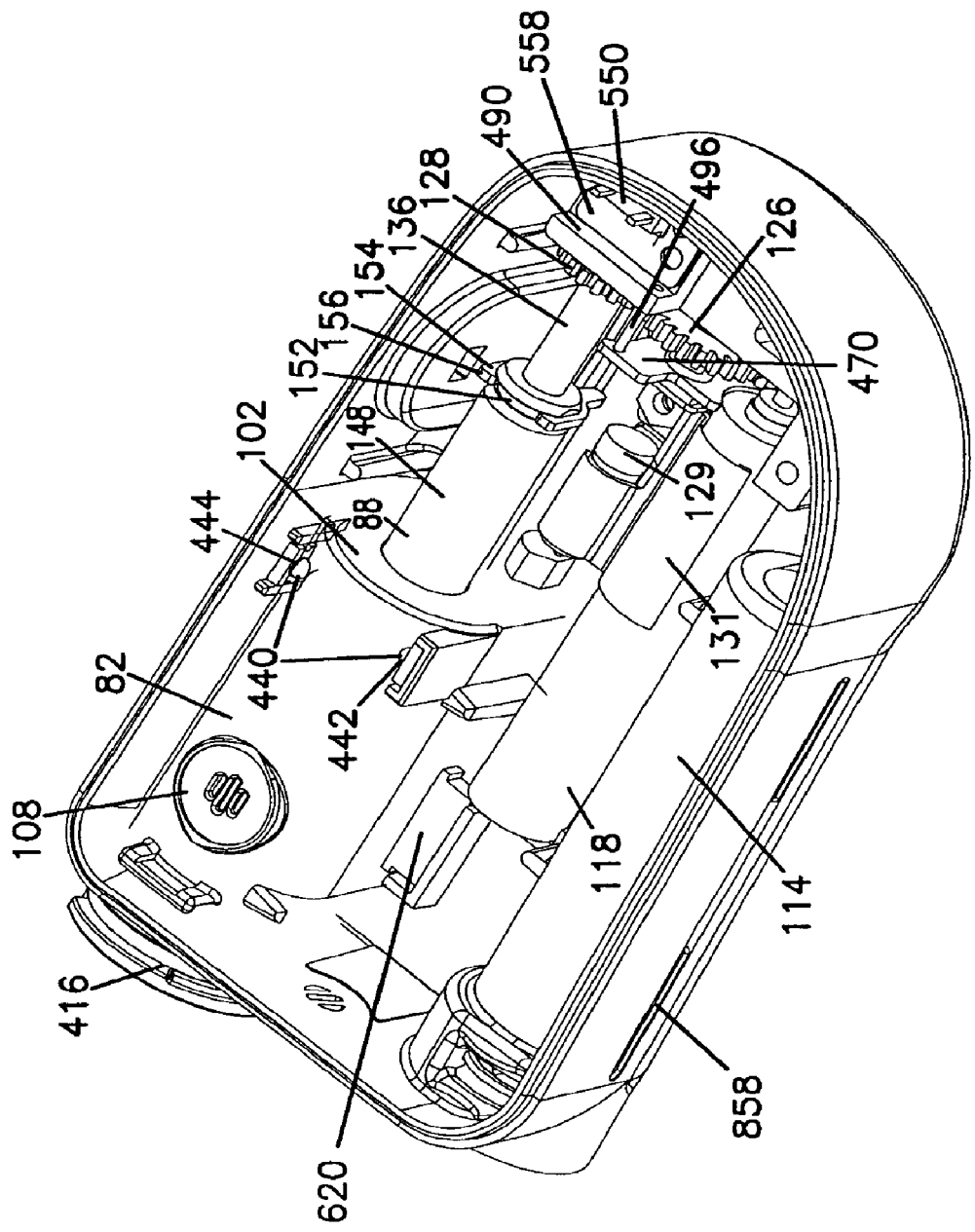
FIG. 29 is a front perspective view of the drive assembly of the pump of FIG. 1.

An infrared (IR) port 620 is in electrical communication with the microprocessor. The IR port 620 may provide data communication with an external device such as a computer for programming an application program, programming pump settings, and downloading historical data logs. The pump 600 can include other types of communication ports in place or in addition to the IR port 620. Examples of other possible communication ports include a radio frequency (RF) port or a port that provides a hard-wired data communication link such as an RS-232 port. The IR port 620 may be located within the pump housing as shown in FIG. 29 and includes an IR emitter and an IR detector. The IR port 620 may be positioned adjacent to two openings 624 and 626 in the pump housing 14, as seen in FIGS. 1 and 4, for allowing communication with the IR emitter and IR detector.

Again referring to FIG. 30, a real-time clock 622 provides a clock signal to the microprocessor 602. An advantage of having a real-time clock 622 is that it provides the program with the actual time in real-time so that the application program can track and control the actual time of day that insulin delivery and other events occur.

A keypad 40 also provides input to the microprocessor 602. Although other possible types of keypads are possible, one type of keypad has four buttons and is a membrane-type of keypad, which provides resistance to water and other environmental conditions. As explained in more detail below, the keypad 40 contains soft keys in that the function of the keys can change as a user executes different menu selections and commands.

Other inputs into the microprocessor 602 include the pressure sensor 550, which is sensitive to the pressure within a reservoir of medication, the cartridge sensor 440 which is sensitive to the presence of a medication cartridge within the medication chamber, and the motion detector or idler gear sensor 468, which detects motion of a gear.

The pump may also include a bolus button 25 for allowing the user to administer a dose of medication. The depression of the bolus button 25 may provide feedback to the user, such as a beep, a tone, or vibration of the pump. The bolus button 25 communicates with the processor 602 to instruct the processor to activate the pump motor 118 so that the drive rod 88 is moved a specified distance, thereby providing the user with a specified dose of medication. The bolus button 25 can be seen within the pump housing 14 in FIG. 1. The bolus button 25 fits within a bolus button cavity 37, best seen in FIG. 2.

Figure 35:
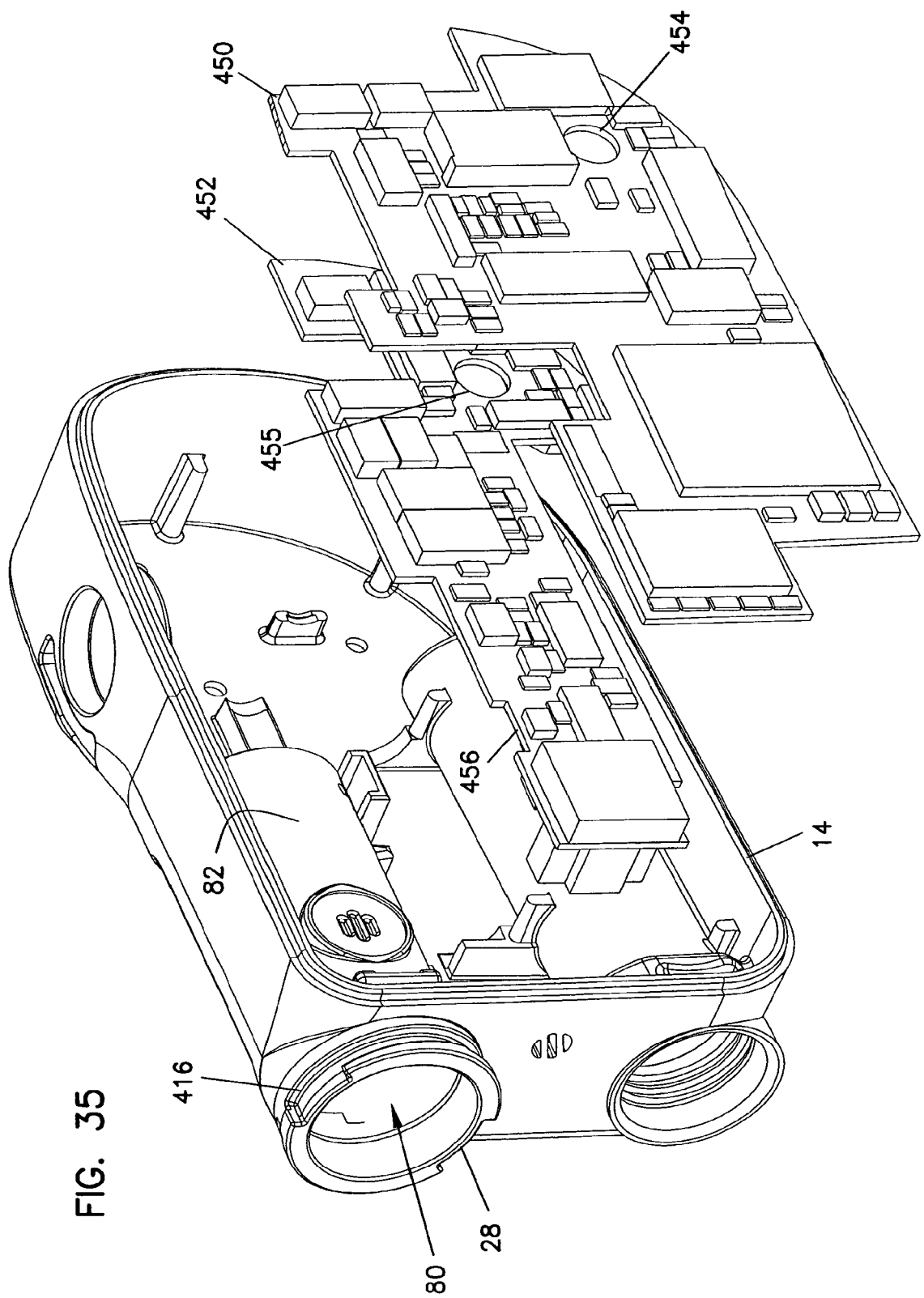
FIG. 35 is a left front perspective view of a pump housing for the pump of FIG. 1 without drive assembly components, where two circuit boards are shown separated from the pump housing.

Many elements of the pump 600 may be positioned within one or more circuit boards within the pump housing 14. For example, the microprocessor 602, the RAM 616, ROM 618, real-time clock 622, and a driver for the display 44 may be positioned on a circuit board. In a preferred embodiment, a top circuit board 450 is positioned above a bottom circuit board 452 within the pump housing 14, as seen in the cross-sectional view of FIG. 22 and the exploded view of FIG. 35. Now referring to FIG. 35, the top circuit board 450 may include an opening 454 and the bottom circuit board 452 may include a corresponding opening 455. The openings 454 and 455 may receive a screw or other connecting structure to allow the circuit boards 450, 452 to be secured to the pump housing 14 via opening 515 in the pump housing 14 (FIG. 1). Preferably, top circuit board 450 is electrically connected to bottom circuit board 452 using a flexible electrical connector. The electrical connector may emerge from the bottom circuit board 452 at the connection location 456 and then attach to the top circuit board 450 at a location above the connect location 456.

Cartridge Detection and Loading Process

The cartridge sensor 440 at the rear most part of the cartridge chamber 80 senses whether the rear edge of the cartridge is positioned at the rear edge of the chamber 80. This information may be used to ensure proper operation of the pump. For example, if the cartridge is removed while the pump is running, an alarm will sound to protect against non-delivery or a free flow of medication. If a cartridge is present in the chamber, but the pump is not programmed to deliver medication, an alarm may be programmed to sound to notify the user that the pump is not running. If no cartridge is present in the cartridge chamber, the user can be notified.

Figure 31:
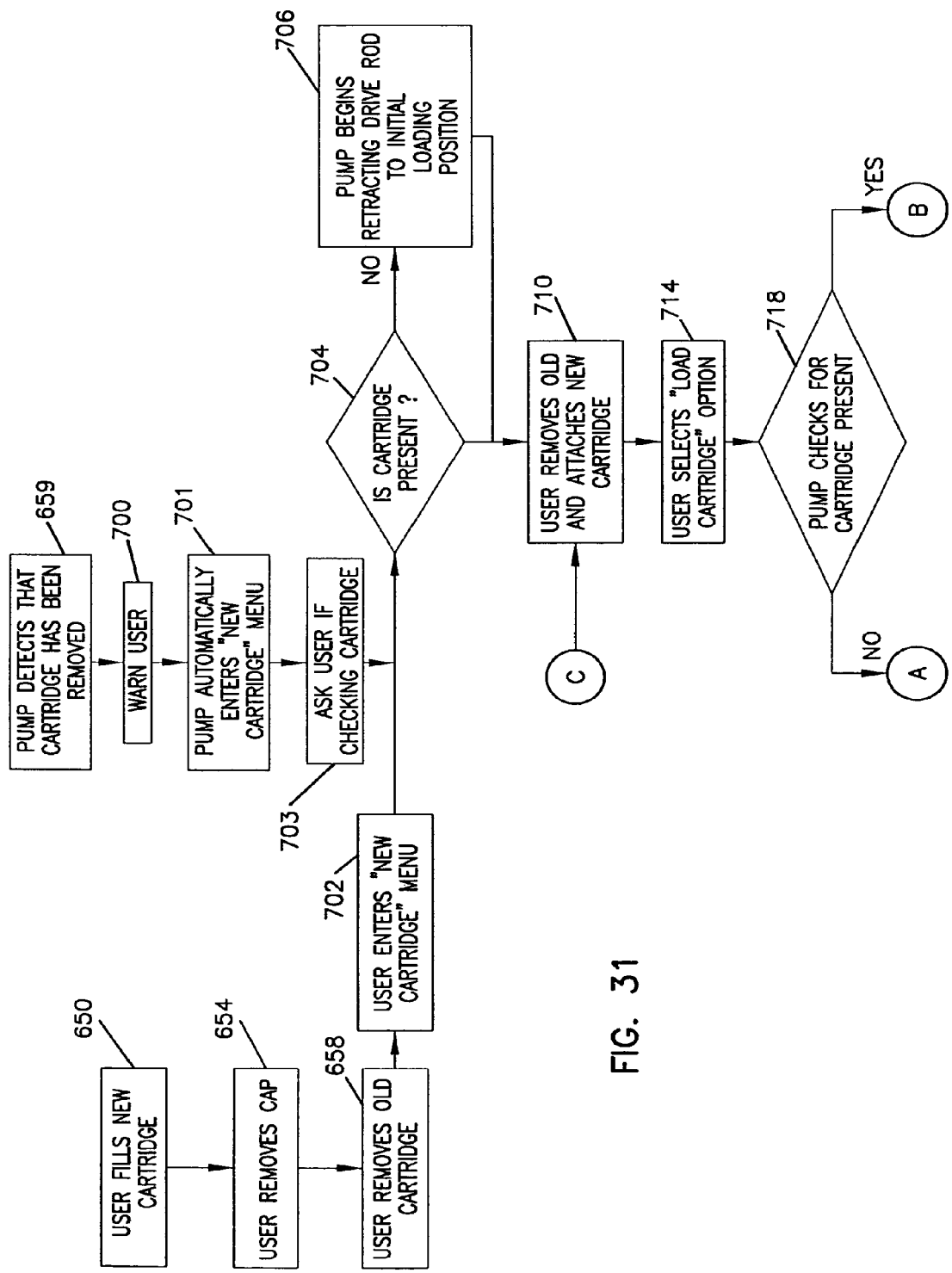
FIG. 31 is a flowchart of the cartridge loading method of one embodiment of the present invention.
Figure 32:
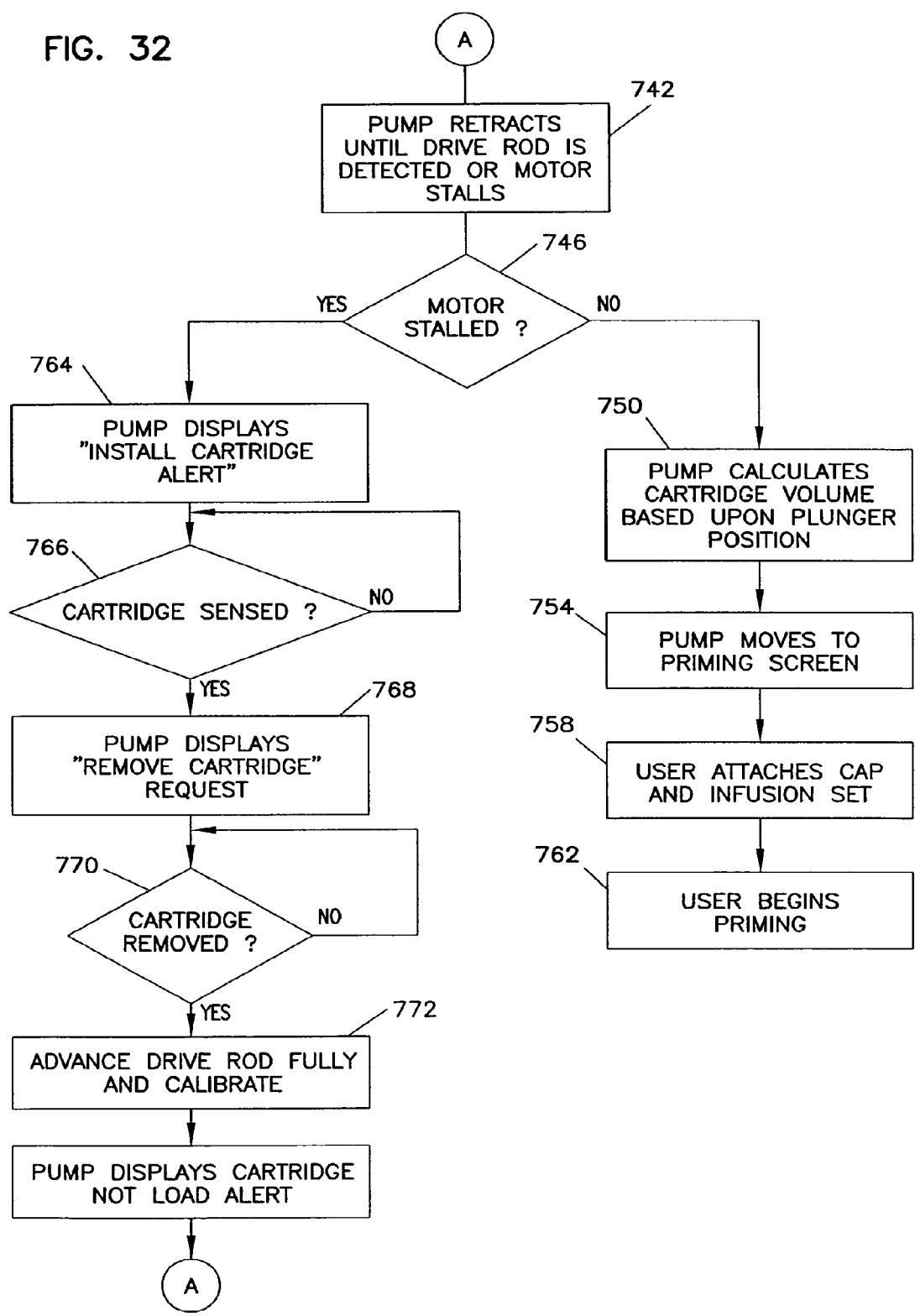
FIG. 32 is a flowchart of further cartridge loading steps of one embodiment of the invention.
Figure 33:
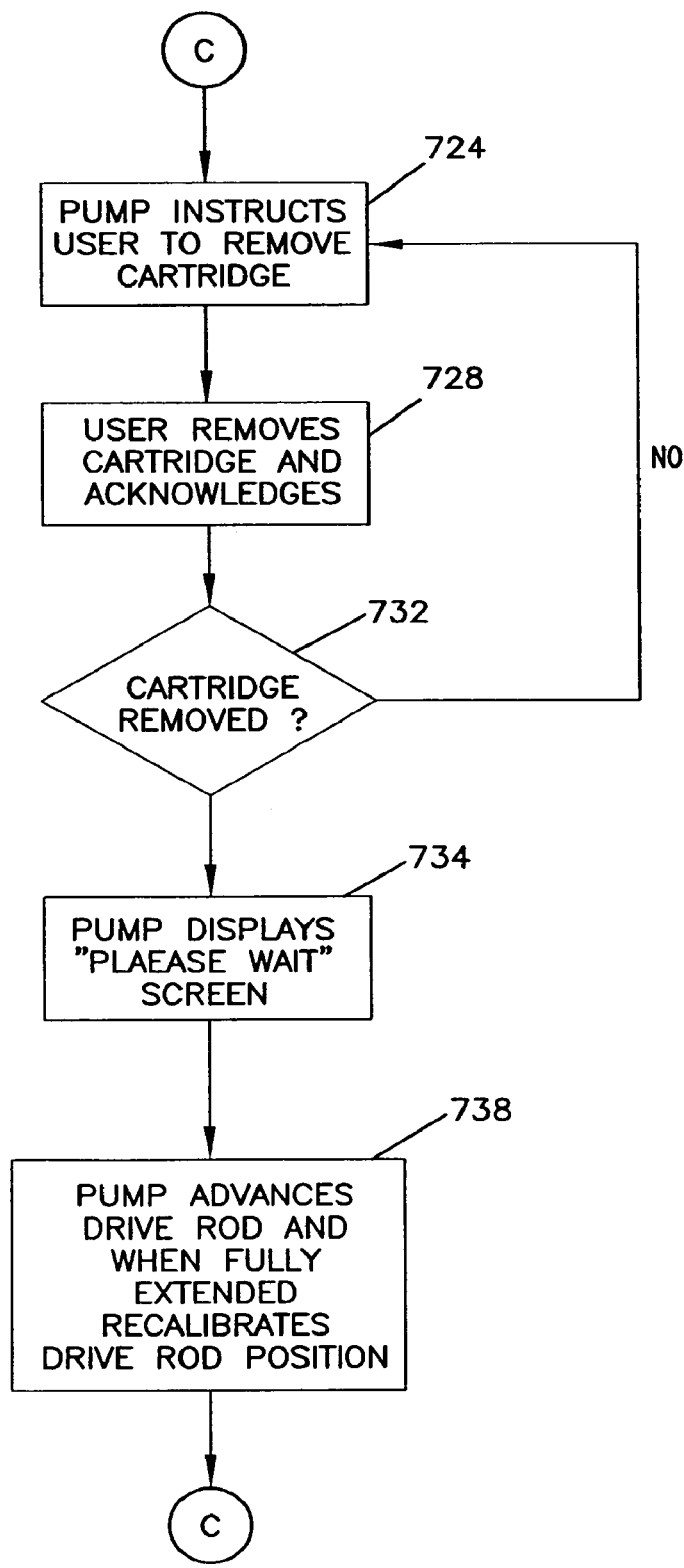
FIG. 33 is a flowchart of additional cartridge loading steps of one embodiment of the present invention.

Information from the cartridge sensor 440 may also facilitate the cartridge loading process. An auto-loading process may be programmed into the pump microprocessor 602 and assist the user in loading the cartridge. Information from the pressure sensor 500 or idler gear sensor 126 may also be used in the cartridge loading process. FIGS. 31-33 are flowcharts illustrating one cartridge loading process. In order to load a new cartridge, first a user fills a new cartridge at step 650 and removes the pump cap 16 at step 654. Any old cartridge already within the chamber 80 is removed at step 658, and the user selects the load cartridge menu at step 702.

Alternatively, the pump may detect when a cartridge is removed as shown in step 659 and automatically enter the new cartridge menu as a result. There are situations where a user will want to remove the cartridge briefly and then put it back in. For example, the user may want to look for air bubbles in the cartridge. In this situation, it may not be necessary to enter the load cartridge menu. The pump may be alert for this situation and not enter the load cartridge menu if a user is removing the cartridge only to check it, not to change it. For example, if the cartridge is more full than a certain threshold level, the pump may assume that the user is checking the cartridge when the cartridge is removed. However, to ensure the user is not unknowingly without medication, the pump may alternatively warn the user and ask the user if she is checking the cartridge or changing the cartridge at step 700. If the user responds that she is checking the cartridge, the pump may maintain the drive rod in the same position, or may slightly extend the drive rod so that it is easy for the user to reattach the drive rod to the cartridge. If the user does not respond or responds that she is changing the cartridge, then the pump may automatically enter the new cartridge menu at step 701. However, to ensure that the cartridge is properly attached to the drive rod after a cartridge is checked, the pump may be programmed to automatically enter the new cartridge menu whenever the cartridge is removed, as shown in FIG. 31. In this case, the pump may query the user at step 703 whether she is checking or changing the cartridge, and may use the answer to that question later in the loading process to determine the best initial loading position for the drive rod.

Once the load cartridge menu is initiated, the pump checks the cartridge sensor 440 to determine if the rear portion of a cartridge is detected at the rear of the chamber at step 704. Typically, no cartridge will be detected at step 704 because the pump has not retracted the new cartridge and the old cartridge has already been removed by the user.

If no cartridge is detected, the motor may be activated to move the drive rod to an initial loading position at step 706. The initial loading position may be fully extended, fully retracted, or somewhere in between, depending on the typical initial plunger position within the cartridge. One preferred initial loading position is between the starting point and the ending point of the distance that the drive rod traveled during delivery of the medication in the previous cartridge. Preferably, the initial loading position is approximately halfway between the starting point and ending point for delivery during the previous cartridge. For example, if the drive rod traveled about 1 inch during delivery of the previous cartridge, the drive rod will be retracted about 0.5 inch at step 706. The automatic retraction of the drive rod to an initial loading position is designed to save the user's time when loading the cartridge. The pump is typically designed to deliver fairly small doses of medication over a long period of time. The full retraction and advancement of the drive rod can therefore take a relatively long period of time. By retracting the drive rod partially, the pump gets a head start on the retraction of the cartridge all the way into the pump.

It is also possible, though not preferred, for the pump to retract fully to the rear of the chamber before the cartridge is loaded. Full retraction is not necessary unless the new cartridge is completely full. If the new cartridge is not completely full, and the drive rod has been fully retracted, the drive rod will have to be advanced in order for the plunger to be attached to the drive rod. Therefore, it is preferable to underestimate the amount that the drive rod will need to be retracted in order to pull the cartridge to the rear of the chamber. In addition, the pump system can take advantage of the fact that most users will fill new cartridges to approximately the level of the previous cartridge. By retracting the drive rod half of this distance, the drive rod is unlikely to be retracted an unnecessary distance.

In determining the initial loading position in step 706, the pump may take into account whether the user removed the previous cartridge in order to install a new cartridge or merely to check the existing cartridge for some reason, such as checking for air bubbles. If the user previously responded at step 703 that they were removing the cartridge to check it, then the initial loading position in step 706 may be the same position or slightly extended from the position it was in when the cartridge was removed.

If a cartridge was detected at step 704, then the user is reminded to make sure that the old cartridge has been removed. If the old cartridge was not already removed, the user does so at step 710. The user attaches the new cartridge to the drive rod interface structure 98 at step 710. The process used to attach a cartridge to the drive rod was previously described. Then the user selects a load cartridge command using the display 44 and keypad 40 at step 714. The cartridge sensor 440 is checked to determine if a cartridge is present at the rear of the chamber at step 718. The pump does not expect a cartridge to be present at the rear of the chamber because the retraction process has not yet been initiated. If no, the steps illustrated in FIG. 32 are followed. If yes, the steps illustrated in FIG. 33 are followed.

If a cartridge is detected at the rear of the chamber in step 718, before the drive rod has retracted beyond the initial loading position, this indicates that possibly the old cartridge was never removed or the cartridge is less full than a minimum amount. Detection of a cartridge at step 718 could also indicate that the new cartridge is considerably less full than the old cartridge, such as less than about half of the previous cartridge. In this situation, the cartridge might have been fully inserted into the chamber without having the plunger engaged with the interface structure 98. For example, if the previously delivered cartridge was initially completely full and all of the medication was delivered, the drive rod traveled the full distance of the cartridge chamber during delivery of that cartridge. The initial loading position of the drive rod for the next cartridge would be halfway extended. However, if the next cartridge was only one-eighth full, the cartridge could be inserted fully in the chamber without contacting the plunger, resulting in detection of a cartridge although the plunger has not yet been attached to the drive rod.

If a cartridge is detected at the rear of the chamber in step 718, the user is prompted to remove the cartridge at step 724. The user then removes the cartridge and acknowledges the removal at step 728. The cartridge sensor 440 is again checked to see if the cartridge has been removed at step 732. If not, the process returns to step 724 where the user is again instructed to remove the cartridge. If the cartridge has been removed, the pump displays a message indicating that the user needs to wait at step 734 while the pump fully advances the drive rod at step 738. By fully advancing the drive rod, the pump ensures that the interface cylinder can be attached to the plunger regardless of the fullness of the cartridge. While the drive rod is fully advanced, the processor recalibrates the fully extended drive rod position to ensure accuracy of future position calculations. The processor also recalibrates the drive rod position when it is fully retracted. After the drive rod is fully advanced at step 738, the user is prompted to attach the new cartridge at step 710 and then selects a load cartridge option at step 714.

The pump may be calibrated to know when the drive rod is at full extension and full retraction. By observing the encoder counts from the motor 118, the intermediate positions of the drive rod may also be calculated. The pump may calculate the beginning position of the drive rod when a cartridge is initially loaded. By knowing the starting position and the intervening encoder counts, the amount of medication expelled from the cartridge may be tracked by the pump.

If a cartridge is not detected at step 718, then the process illustrated in FIG. 32 is followed. The pump retracts the drive rod at step 742, which should now be attached to the plunger of the cartridge, until the rear of the cartridge is detected by the cartridge sensor 440, the motor stalls, or the drive rod is fully retracted. The pump may also use the pressure sensor 550 to determine when the drive rod is fully retracted where the pressure sensor is pre-loaded to detect negative pressures on the drive rod. If the cartridge is detected, the pump calculates the cartridge volume based on how far the drive rod was retracted before a cartridge was detected at step 750. The pump begins a priming program, and prompts the user to attach the pump cap 16 and an infusion set to the delivery end of the cartridge at step 754. Once the cap and an infusion set are attached at step 758, the user initiates the priming process at step 762.

If at step 746, the motor stalled or the drive rod was determined to be fully retracted through other detection methods before a cartridge was detected, then the pump displays an install cartridge alert at step 764. If this occurs, two possible causes would be that the user never inserted a new medication pump or the cartridge sensor is not functioning properly. The cartridge sensor is again checked at step 766. If a cartridge is detected, the user is instructed to remove the cartridge at step 768 to confirm that the cartridge sensor is working properly. The pump checks for a state change at the cartridge sensor at step 770 to confirm that the cartridge was removed. If the cartridge was removed, the pump fully advances the drive rod and recalibrates the drive rod position when it is fully extended at step 772. Because of the preceding cartridge sensor checks, the system ensures that there is no cartridge sensor in the chamber when the drive rod is fully advanced. The process then returns to step 710 on FIG. 31 where the user is prompted to attach a new cartridge.

Child Safety Cap

Figure 38:
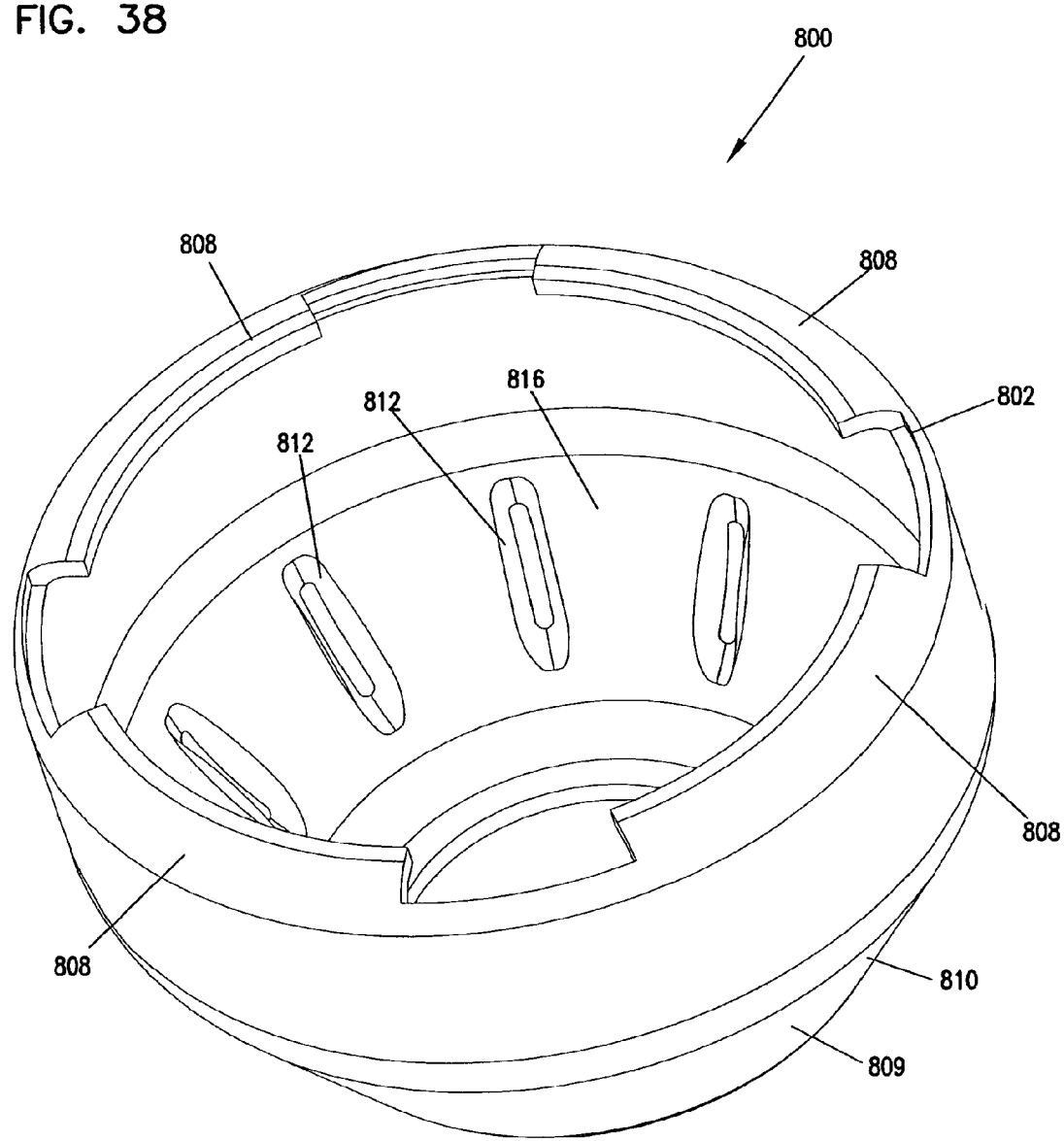
FIG. 38 is a bottom perspective view of a child safety pump cap cover according to one embodiment of the present invention.
Figure 39:
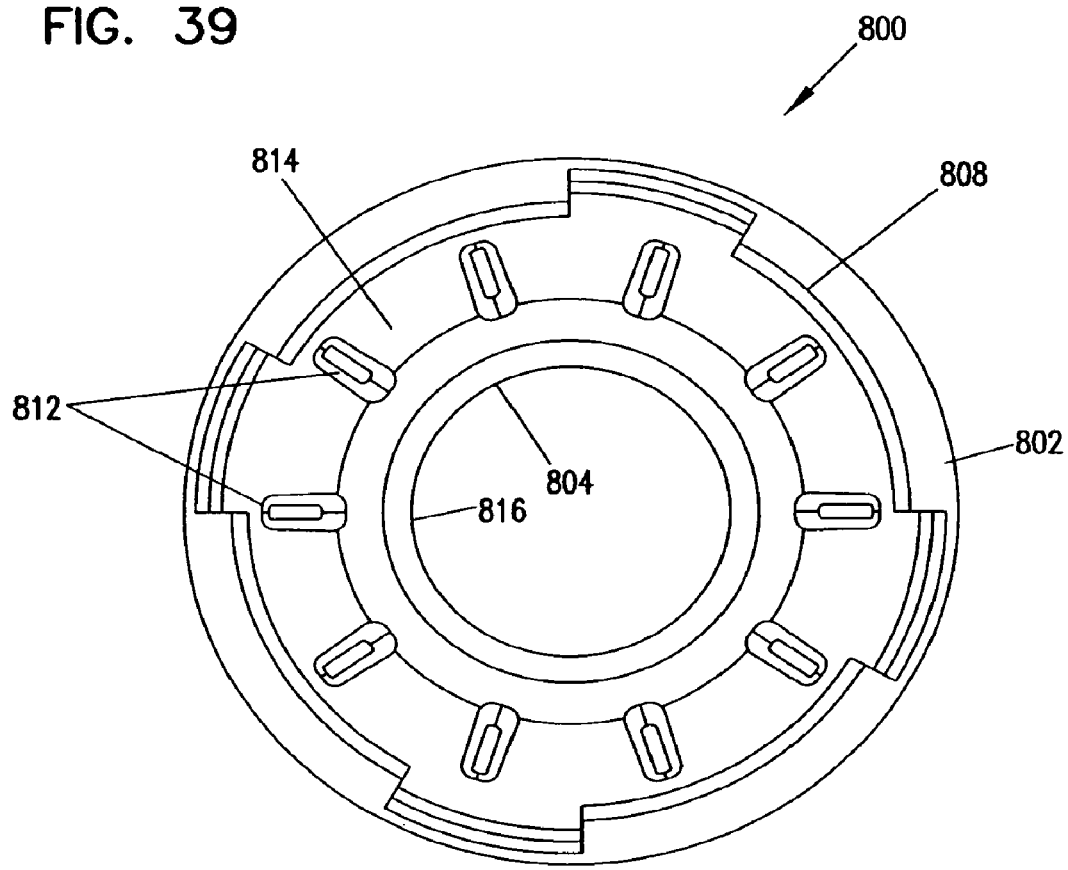
FIG. 39 is a bottom view of the child safety pump cap cover of FIG. 38.
Figure 40:
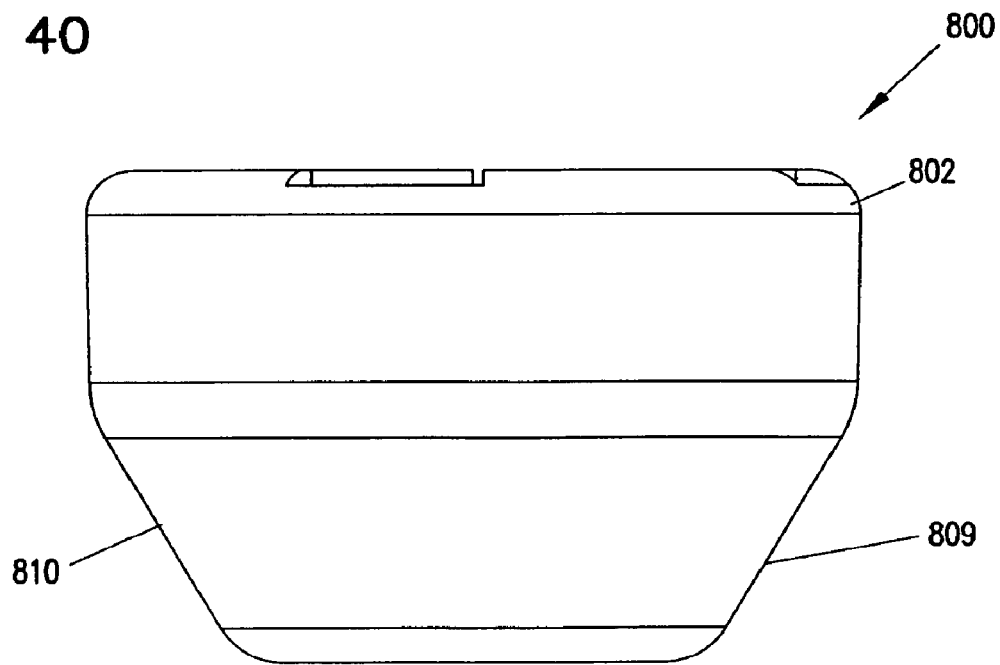
FIG. 40 is a side view of the child safety pump cap cover of FIG. 38.

It may be desirable to configure the pump cap 16 to require some dexterity and strength to operate, so that it is difficult for a young child to open the cap. Now referring to FIGS. 38-40, in one embodiment, a safety cap cover 800 may be configured to snap over the standard pump cap 16. The pump cap 16 is illustrated in FIGS. 1 and 17-20. The cap cover 800 may have a first pump end 802 and a second delivery end 804. At both ends, the cap cover 800 preferably defines openings to allow passage of an infusion set for attachment to the user. At the attachment end 802, a lip 808 may be included that can fit around the pump end 410 of the pump cap 16. The lip 808 may be discontinuous, as illustrated in FIG. 38, to facilitate snapping the cap cover 800 over the pump cap 16 and removing it when it is no longer desired. A wall 809 extends between the pump end 802 and the second delivery end 804, including a first portion 810 of the wall that has a truncated cone shape. The wall of the first portion 810 is preferably sufficiently flexible so that an adult of normal strength can squeeze the first portion 810 of the cap cover to apply torque to the pump cap 16. When the wall of the first portion 810 is squeezed, the cap cover 800 moves between a first shape or state and a second shape or state. In the first state, the cover 800 rotates freely around the pump cap 16. In the second state, the safety cap cover contacts the exterior surface of the pump cap so that the cap cover 800 does not rotate freely. In the second state or position, the user may apply torque to the pump cap 16 through the cap cover 800. Alternatively, the pump cap may be configured so that the user can press down on the cap cover 800 while turning the cap cover 800 to apply torque to the pump cap 16.

Structures on the pump cap 16 or the cap cover 800 can facilitate the rotation of the pump cap 16. For example, the gripping structures 422 on the exterior surface of the pump cap 16 shown in FIG. 17 may make it easier for the user to grip the pump cap surface through the cap cover 800. Preferably, the gripping structures 422 are constructed of an elastomeric material. Alternatively, or in combination with the gripping structures 422, mating gripping structures 812 may be included on an internal surface 814 of the first portion 810 of the wall 809 of the cap cover, as shown in FIG. 38. The inclusion of gripping structures on the cap cover, pump cap, or both, prevent the cap cover from slipping as it is pressed against the pump cap.

In an alternative embodiment of a pump cap that is difficult for children to open, an outer shell similar to the cap cover 800 is integral with the pump cap 16. The outer shell may rotate freely on the pump cap unless the outer shell is squeezed or pressed down while it is turned.

Belt Clip Attachment

Figure 36:
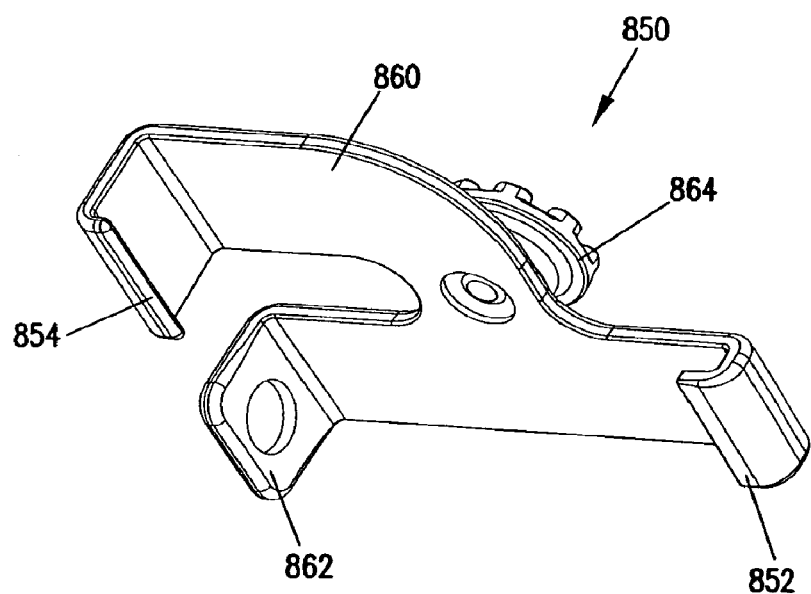
FIG. 36 is a front perspective view of one embodiment of a pump clip for attachment to the pump of FIG. 1, according to the present invention.
Figure 37:
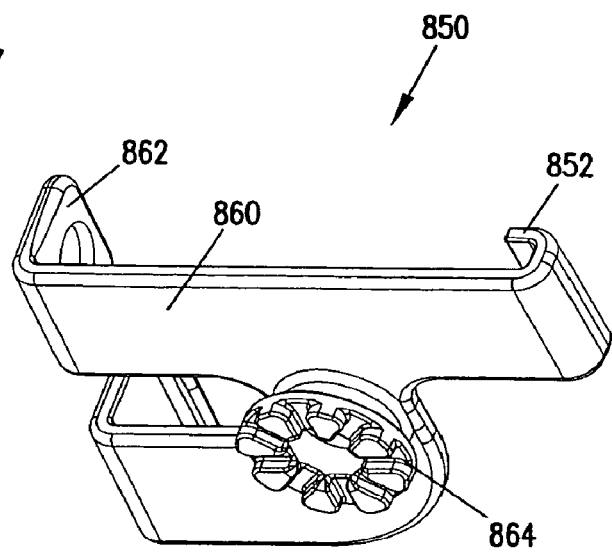
FIG. 37 is a rear perspective view of the pump clip of FIG. 36.

An attachment device may be provided and used with the pump 10 that is useful for attaching the pump to a belt clip or another holding device. One example of a belt clip attachment device 850 is shown in FIGS. 36-37. The attachment device 850 includes a first protrusion 852 and a second protrusion 854. The first protrusion 852 is configured to be inserted into a first slot 856 on the top of the pump housing 14, as shown in FIG. 1. The second protrusion 854 is configured to be inserted into a second slot 858 on the bottom portion of the housing 14 as shown in FIG. 29. A main body portion 860 of the attachment device 850 rests against the back side of the pump housing 14, opposite the display area. The attachment device 850 may also include a third protrusion 862 that can be used to further support the pump 14 within the attachment 850. The device 850 may also include a pivot point 864. The pivot point may be the point of attachment between the attachment device 850 and another structure, such as a belt clip. The pivot point 864 may allow the body 860 of the attachment device 850 to rotate with respect to the other device to which it is attached. This rotation allows for maximum comfort of the pump user. For example, if the pump 10 is attached to a belt clip using the clip attachment device 850, then the pump may be rotated to the optimal position when the user is seated. The pivot point may be positionable between several discrete positions. Belt clips that can receive a pivot point similar to pivot point 864 are well known.

Alternatively, the pump may be positionable in one of several orientations in the belt clip, but may not be allowed to rotate freely between those positions. Free rotation of the pump may cause kinking of the tube. In this scenario, the user would remove the attachment device from the belt clip in order to move the pump to a different orientation relative to the belt clip.

The various embodiments described above are provided by way of illustration only and should not be construed to limit the invention. Those skilled in the art will readily recognize various modifications and changes which may be made to the present invention without strictly following the exemplary embodiments and applications illustrated and described herein and without departing from the true spirit and scope of the present invention which is set forth in the following claims.

What is claimed is:

1. A medication pump, comprising:
   a housing including an external wall and a plurality of internal adjoining housings, including a first housing enclosing a cartridge and a second housing;
   a primary vent for venting gas between the medication pump and atmosphere outside the medication pump, the primary vent including a primary liquid barrier allowing passage of gas therethrough while preventing passage of liquid therethrough; and
   a secondary vent on the first housing for internally venting gas between the first housing and the second housing, the secondary vent including a secondary liquid barrier allowing passage of gas therethrough to an interior of the housing while preventing passage of liquid therethrough.

2. The medication pump of claim 1, wherein the housing further comprises a third housing enclosing a battery.

3. The medication pump of claim 1, wherein the primary liquid barrier is attached to the housing a pressure sensitive adhesive.

4. The medication pump of claim 1, wherein the cartridge is replaceable.

5. The medication pump of claim 1, wherein the first housing is liquid sealed from a remainder of the medication pump.

6. A medication pump, comprising:
   an outer housing defining an interior with one or more walls coupled to the housing that divide the interior into at least first and second chambers, the first chamber being a cartridge chamber including a drive rod extending therein, the drive rod configured to couple to a plunger of a cartridge; and
   an interior vent formed between the first and second chambers, the interior vent including a liquid barrier allowing passage of gas between the first and second chambers while preventing passage of liquid therethrough.

7. The medication pump of claim 6, wherein the housing includes an exterior vent formed on the housing for venting to atmosphere, the exterior vent including a liquid barrier allowing passage of gas therethrough while preventing passage of liquid therethrough.

8. The medication pump of claim 7, wherein the first chamber is a cartridge chamber sized to receive a cartridge containing a medication, and the second chamber forms an open interior of the outer housing.

9. The medication pump of claim 8, wherein the exterior vent is formed between the open interior and the atmosphere.

10. The medication pump of claim 6, wherein the cartridge is replaceable.

11. The medication pump of claim 6, wherein the cartridge chamber is liquid sealed with respect to the second chamber of the housing.

12. The medication pump of claim 6, further comprising a battery chamber positioned in the housing, the battery chamber being sized to enclose a battery.

13. The medication pump of claim 6, wherein the liquid barrier of the interior vent is attached to the first chamber using a pressure sensitive adhesive.

14. A method of venting a medication pump, the method comprising:
   forming an interior vent between first and second chambers defined by a wall in an interior of a housing of the medication pump, the interior vent including a liquid barrier allowing passage of gas between the first and second chambers while preventing passage of liquid therethrough;
   forming the first chamber as a cartridge chamber including a drive rod extending therein, the drive rod configured to couple to a plunger of a cartridge; and
   allowing gas to pass through the interior vent from the first chamber to the second chamber.

15. The method of claim 14, further comprising:
   forming an exterior vent in the housing of the medication pump, the exterior vent including a liquid barrier allowing passage of gas therethrough while preventing passage of liquid therethrough; and allowing gas to pass through the exterior vent to atmosphere.

16. The method of claim 15, further comprising:
forming the first chamber as a cartridge chamber sized to receive a cartridge containing a medication, and the second chamber as an open interior of the housing; and
allowing gas to pass from the open interior through the exterior vent and to the atmosphere.

17. The method of claim 14, further comprising sealing the cartridge chamber from the second chamber of the housing.

18. The method of claim 14, further comprising attaching the liquid barrier of the interior vent to the second chamber using a pressure sensitive adhesive.

* * * * *

UNITED STATES PATENT AND TRADEMARK OFFICE
CERTIFICATE OF CORRECTION

| | | |
|---|---|---|
| PATENT NO. | : 7,905,859 B2 | Page 1 of 1 |
| APPLICATION NO. | : 11/680871 | |
| DATED | : March 15, 2011 | |
| INVENTOR(S) | : Bynum et al. | |

It is certified that error appears in the above-identified patent and that said Letters Patent is hereby corrected as shown below:

<u>Figure 33, No. 734</u>:
Delete "PLAEASE" and insert -- PLEASE --.

<u>Column 3, Line 25</u>:
Delete "a attaching" and insert -- attaching a --.

Signed and Sealed this
Twenty-first Day of June, 2011

David J. Kappos
*Director of the United States Patent and Trademark Office*